United States Patent
Kanada

(10) Patent No.: US 10,930,396 B2
(45) Date of Patent: Feb. 23, 2021

(54) SIMILAR CASE SEARCH APPARATUS, METHOD FOR OPERATING SIMILAR CASE SEARCH APPARATUS, AND SIMILAR CASE SEARCH SYSTEM

(71) Applicant: FUJIFILM Corporation, Tokyo (JP)

(72) Inventor: Shoji Kanada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 21 days.

(21) Appl. No.: 16/440,830

(22) Filed: Jun. 13, 2019

(65) Prior Publication Data

US 2019/0295724 A1 Sep. 26, 2019

Related U.S. Application Data

(63) Continuation of application No. PCT/JP2017/041768, filed on Nov. 21, 2017.

(30) Foreign Application Priority Data

Dec. 19, 2016 (JP) .............................. JP2016-245304

(51) Int. Cl.
*G16H 50/20* (2018.01)
*G16H 50/70* (2018.01)
(Continued)

(52) U.S. Cl.
CPC .............. *G16H 50/20* (2018.01); *A61B 6/03* (2013.01); *G06F 16/55* (2019.01); *G06Q 50/22* (2013.01);
(Continued)

(58) Field of Classification Search
None
See application file for complete search history.

(56) References Cited

U.S. PATENT DOCUMENTS 10,734,107 B2* 8/2020 Osawa ................ G06F 16/5838
2004/0184644 A1* 9/2004 Leichter ................. G16H 30/40
382/128
(Continued)

FOREIGN PATENT DOCUMENTS

JP 2009-095550 A 5/2009
JP 2010-017274 A 1/2010
(Continued)

OTHER PUBLICATIONS

International Search Report issued in PCT/JP2017/041768; dated Feb. 13, 2018.
(Continued)

*Primary Examiner* — Delomia L Gilliard
(74) *Attorney, Agent, or Firm* — Studebaker & Brackett PC

(57) ABSTRACT

A weighting processing unit performs a weighting process for an individual lesion similarity which is a similarity between a target lesion and a case lesion of the same type, using a first weighting coefficient corresponding to the degree of contribution of each type of lesion to the specification of a disease name, to calculate a processed individual lesion similarity corresponding to a first purpose of specifying the disease name. In addition, the weighting processing unit performs the weighting process for the individual lesion similarity, using a second weighting coefficient corresponding to the degree of contribution of each type of lesion to the specification of a severity, to calculate a processed individual lesion similarity corresponding to a second purpose of specifying the severity. A total similarity between a target image and a case image is calculated for each purpose on the basis of the processed individual lesion similarities.

10 Claims, 21 Drawing Sheets

(51) Int. Cl.
*G16H 30/40* (2018.01)
*G06T 7/00* (2017.01)
*G16H 30/00* (2018.01)
*G06F 16/55* (2019.01)
*A61B 6/03* (2006.01)
*G06Q 50/22* (2018.01)
*G16H 10/00* (2018.01)

(52) U.S. Cl.
CPC ........... *G06T 7/0014* (2013.01); *G16H 10/00* (2018.01); *G16H 30/00* (2018.01); *G16H 30/40* (2018.01); *G16H 50/70* (2018.01)

(56) References Cited

U.S. PATENT DOCUMENTS

| | | | |
|---|---|---|---|
| 2010/0014756 A1 | 1/2010 | Kato et al. | |
| 2010/0076921 A1 | 3/2010 | Kato et al. | |
| 2010/0250275 A1* | 9/2010 | Sakagawa | G16H 50/70 705/2 |
| 2013/0006087 A1* | 1/2013 | Kondo | G16H 30/20 600/407 |
| 2013/0114867 A1* | 5/2013 | Kondo | G06F 19/321 382/128 |
| 2013/0259350 A1* | 10/2013 | Sato | G06T 7/0014 382/131 |
| 2014/0089000 A1* | 3/2014 | Takata | G16H 50/70 705/2 |
| 2017/0011199 A1* | 1/2017 | Oosawa | G06F 19/321 |
| 2019/0131012 A1* | 5/2019 | Osawa | G06T 7/0012 |
| 2020/0074621 A1* | 3/2020 | Kanada | G06T 7/0012 |

FOREIGN PATENT DOCUMENTS

| | | |
|---|---|---|
| JP | 2010-079398 A | 4/2010 |
| JP | 2011-118540 A | 6/2011 |
| JP | 2015-191285 A | 11/2015 |

OTHER PUBLICATIONS

International Preliminary Report on Patentability and Written Opinion issued in PCT/JP2017/041768; dated Jun. 25, 2019.

Akira Oosawa; Development of "SYNAPSE Case Match", content-based image retrieval system for supporting Lung Cancer diagnosis; IEICE Technical Report; Jan. 17, 2013; pp. 207-209; vol. 112, No. 411.

The extended European search report issued by the European Patent Office dated Oct. 2, 2019, which corresponds to EP17883082.4-1217 and is related to U.S. Appl. No. 16/440,830.

* cited by examiner

| CASE ID | CASE IMAGE | CASE LESION INFORMATION ||| DISEASE NAME | SEVERITY |
| --- | --- | --- | --- | --- | --- | --- |
| | | LESION ID | TYPE | FEATURE AMOUNT | | |
| C001 | F001-1 TO 20 | L001 | GROUND-GLASS OPACITY | ZC11, ZC21, ZC31, ... | BACTERIAL PNEUMONIA | MILD LEVEL |
| | | L002 | INFILTRATIVE SHADOW | ZC12, ZC22, ZC32, ... | | |
| | | ⋮ | | ⋮ | | |

FIG. 9

| | WEIGHTING COEFFICIENT TABLE (DISEASE NAME: HYPERSENSITIVE PNEUMONIA) | |
| | WEIGHTING COEFFICIENT TABLE (DISEASE NAME: BACTERIAL PNEUMONIA) | |
| | WEIGHTING COEFFICIENT TABLE (DISEASE NAME: INTERSTITIAL PNEUMONIA) | |

| TYPE | FIRST WEIGHTING COEFFICIENT CF1 (FIRST PURPOSE) | SECOND WEIGHTING COEFFICIENT CF2 (SECOND PURPOSE) |
|---|---|---|
| INFILTRATIVE SHADOW | 0.25 | 2.0 |
| MASS SHADOW | 1.0 | 2.0 |
| GROUND-GLASS OPACITY | 1.5 | 1.5 |
| NODULAR SHADOW | 1.0 | 1.0 |
| RETICULAR SHADOW | 1.5 | 1.5 |
| LINEAR SHADOW | 0.5 | 1.0 |
| HONEYCOMB LUNG | 1.5 | 2.0 |
| CYST | 0.5 | 1.0 |
| EMPHYSEMA | 0.25 | 1.0 |
| ⋮ | ⋮ | ⋮ |

56

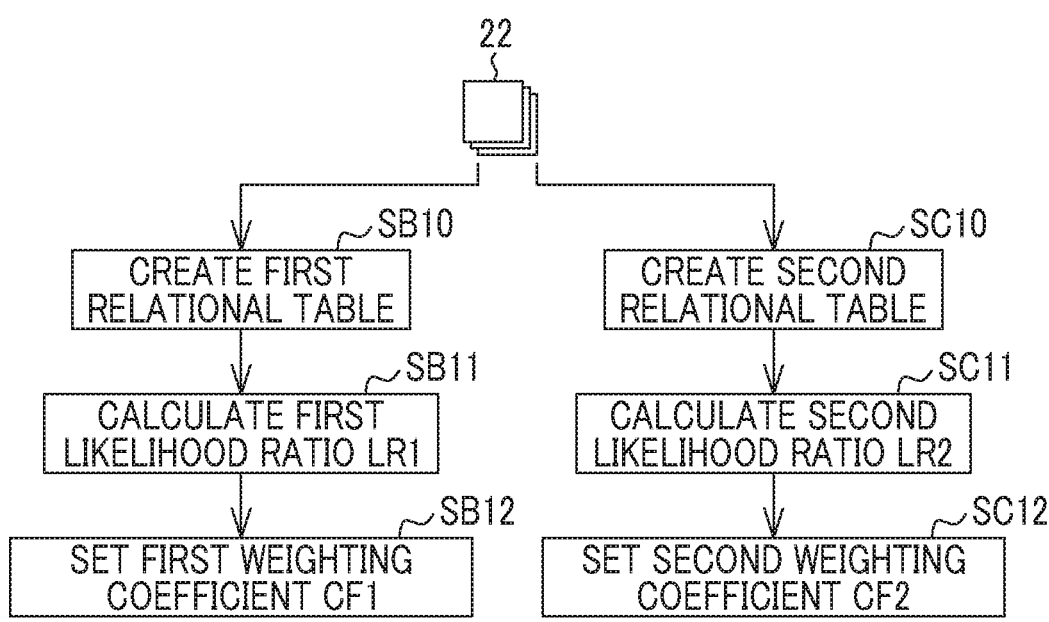

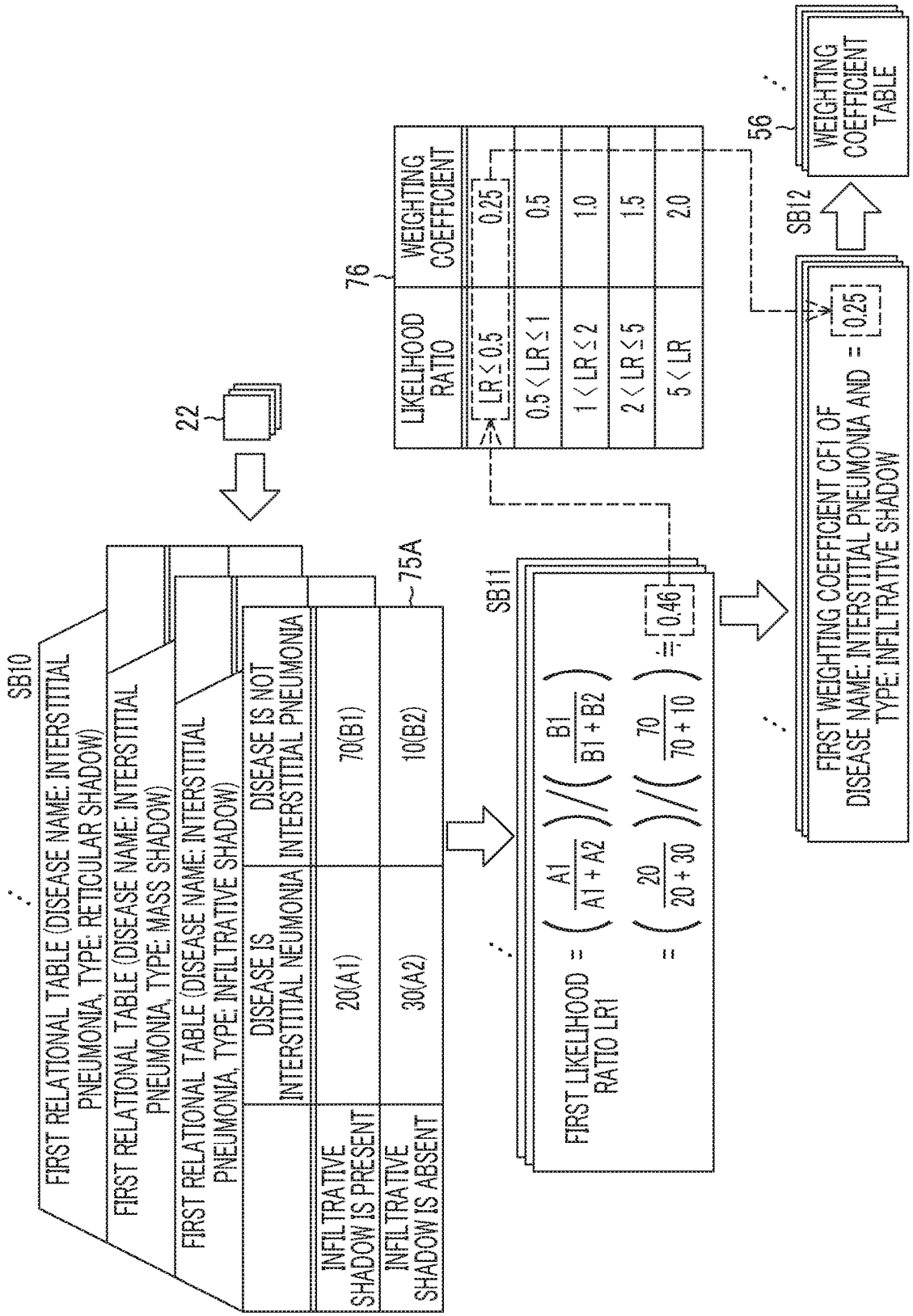

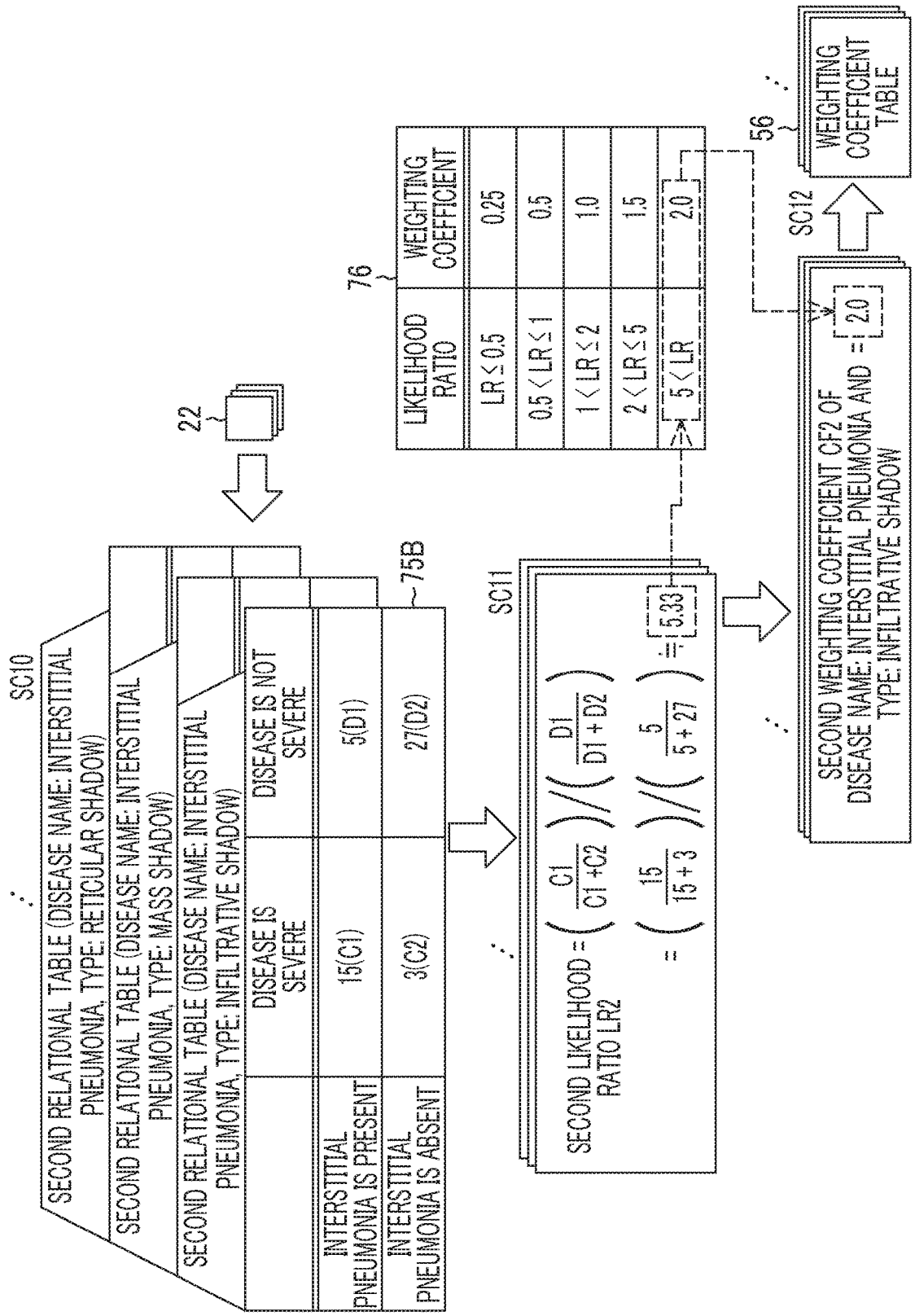

FIG. 16

| CASE ID | DISEASE NAME | SEVERITY | TOTAL SIMILARITY TS-1 (FIRST PURPOSE) | RANKING (FIRST PURPOSE) | TOTAL SIMILARITY TS-2 (SECOND PURPOSE) | RANKING (SECOND PURPOSE) |
|---|---|---|---|---|---|---|
| C001 | BACTERIAL PNEUMONIA | MILD | 17.2 | 4 | 12.7 | 3 | 2 |
| C005 | BACTERIAL PNEUMONIA | MILD | 15.7 | 3 | 11.9 | 2 | 1 |
| C008 | BACTERIAL PNEUMONIA | MILD | 20.8 | 6 | 26.4 | 9 | 3 |
| C012 | TUBERCULOSIS | MILD | 22.5 | 9 | 22.9 | 8 | 2 |
| C033 | TUBERCULOSIS | MILD | 18.6 | 5 | 18.6 | 6 | 1 |
| C048 | TUBERCULOSIS | SEVERE | 30.8 | 12 | 29.3 | 11 | 3 |
| C053 | HYPERSENSITIVE PNEUMONIA | MILD | 9.1 | 1 | 13.1 | 4 | 2 |
| C062 | HYPERSENSITIVE PNEUMONIA | MILD | 12.5 | 2 | 10.3 | 1 | 1 |
| C081 | HYPERSENSITIVE PNEUMONIA | SEVERE | 21.5 | 7 | 16.5 | 5 | 3 |
| C088 | INTERSTITIAL PNEUMONIA | MILD | 21.6 | 8 | 28.3 | 10 | 2 |
| C094 | INTERSTITIAL PNEUMONIA | MILD | 23.7 | 10 | 19.1 | 7 | 1 |
| C100 | INTERSTITIAL PNEUMONIA | SEVERE | 28.1 | 11 | 30.5 | 12 | 3 |

FIG. 17
| CANDIDATE DISEASE RANKING | DISEASE NAME | TOTAL SIMILARITY TS-1 (REPRESENTATIVE VALUE) | CASE IMAGE (REPRESENTATIVE IMAGE) |
|---|---|---|---|
| 1 | HYPERSENSITIVE PNEUMONIA | 9.1 | 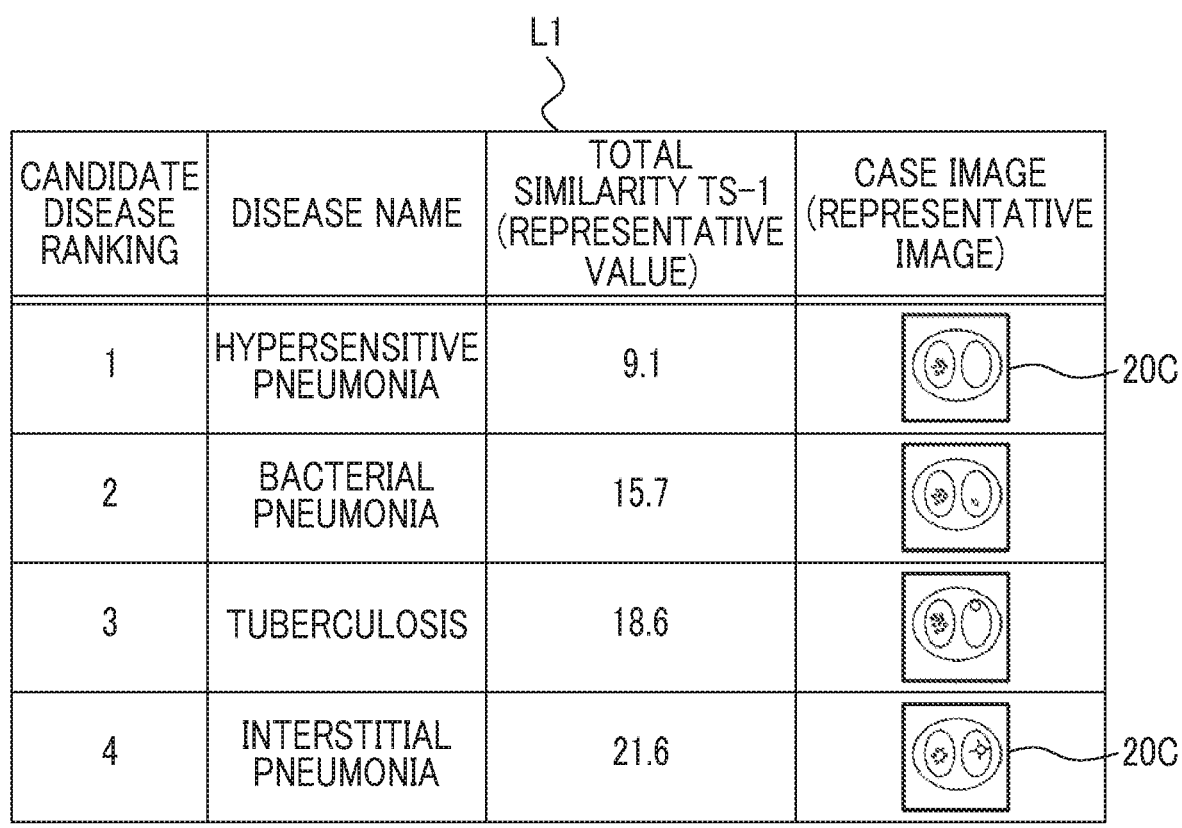 —20C |
| 2 | BACTERIAL PNEUMONIA | 15.7 | 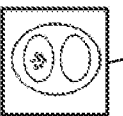 |
| 3 | TUBERCULOSIS | 18.6 | 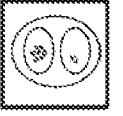 |
| 4 | INTERSTITIAL PNEUMONIA | 21.6 | 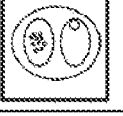 —20C |
L1

FIG. 18
| DISEASE NAME | RANKING IN SAME DISEASE | CASE ID | TOTAL SIMILARITY TS-2 | SEVERITY | CASE IMAGE |
|---|---|---|---|---|---|
| HYPERSENSITIVE PNEUMONIA | 1 | C062 | 10.3 | MILD |  |
| | 2 | C053 | 13.1 | MILD |  |
| | 3 | C081 | 16.5 | SEVERE |  |
| BACTERIAL PNEUMONIA | 1 | C005 | 11.9 | MILD |  |
| | 2 | C001 | 12.7 | MILD |  |
| | 3 | C008 | 26.4 | MILD |  |
| TUBERCULOSIS | 1 | C033 | 18.6 | MILD |  |
| | 2 | C012 | 22.9 | MILD |  |
| | 3 | C048 | 29.3 | SEVERE |  |
| INTERSTITIAL PNEUMONIA | 1 | C094 | 19.1 | MILD |  |
| | 2 | C088 | 28.3 | MILD |  |
| | 3 | C100 | 30.5 | SEVERE |  |

FIG. 20

LIST DISPLAY SCREEN ~85

LIST 1 FOR EACH PURPOSE (SPECIFICATION OF DISEASE NAME) ~L1

| CANDIDATE DISEASE RANKING | DISEASE NAME | SIMILARITY CORRESPONDING TO PURPOSE OF SPECIFYING DISEASE NAME |
|---|---|---|
| 1 | HYPERSENSITIVE PNEUMONIA | 9.1 |
| 2 | BACTERIAL PNEUMONIA | 15.7 |
| 3 | TUBERCULOSIS | 18.6 |
| 4 | INTERSTITIAL PNEUMONIA | 21.6 |

LIST 2 FOR EACH PURPOSE (SPECIFICATION OF SEVERITY) ~L2

| RANKING IN SAME DISEASE | CASE ID | SIMILARITY CORRESPONDING TO PURPOSE OF SPECIFYING SEVERITY | SEVERITY | CASE IMAGE |
|---|---|---|---|---|
| 1 | C062 | 10.3 | MILD | |
| 2 | C053 | 13.1 | MILD | |
| 3 | C081 | 16.5 | SEVERE | |

RE-SEARCH ~88    END ~87

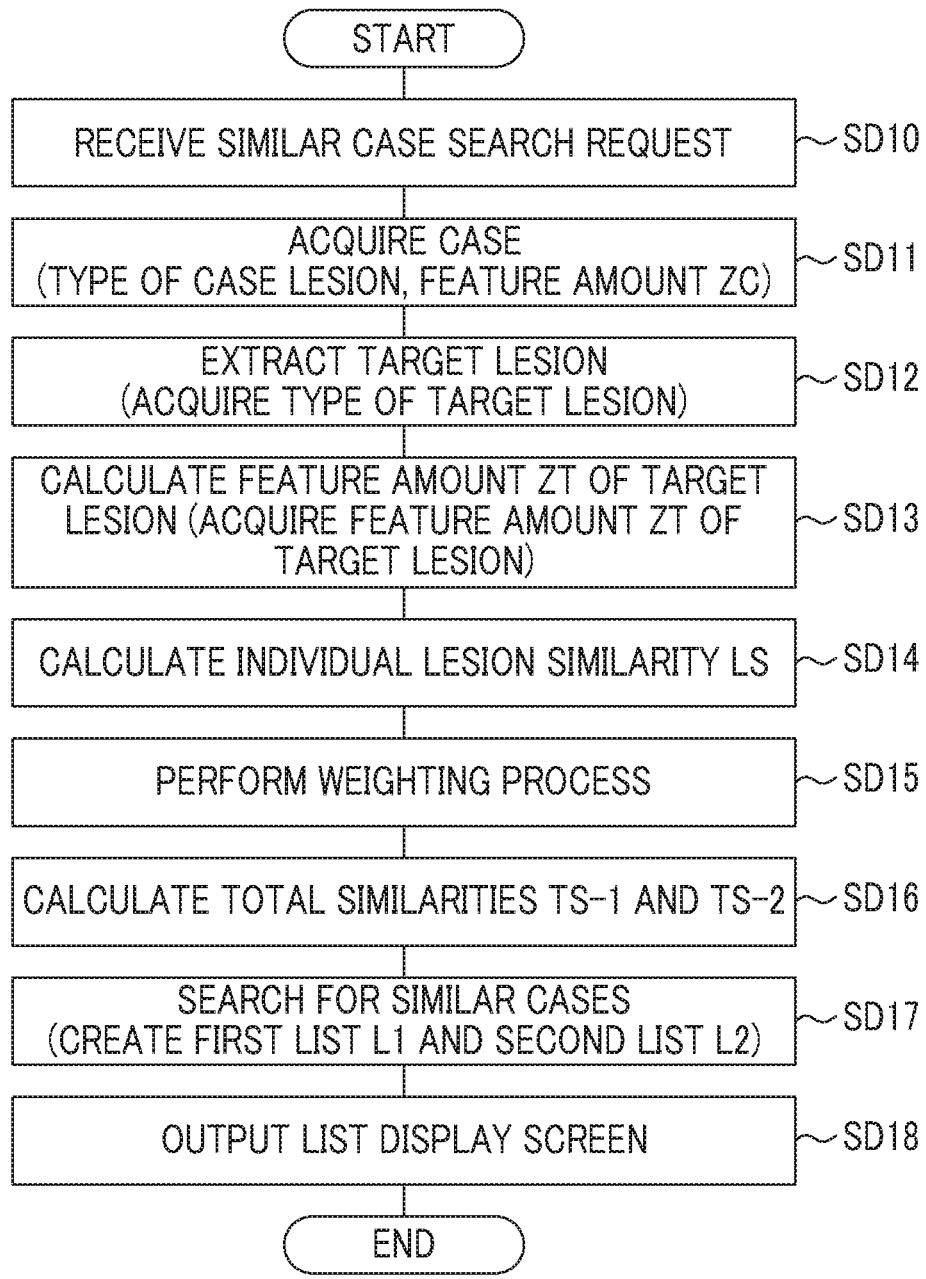

FIG. 22

FIRST RELATIONAL TABLE 95A
(DISEASE NAME: INTERSTITIAL PNEUMONIA, TYPE: INFILTRATIVE SHADOW)

| TYPE | DISEASE IS INTERSTITIAL PNEUMONIA | DISEASE IS NOT INTERSTITIAL PNEUMONIA |
|---|---|---|
| LARGE INFILTRATIVE SHADOW IS PRESENT | 2(A1) | 44(B1) |
| MEDIUM INFILTRATIVE SHADOW IS PRESENT | 6(A2) | 16(B2) |
| SMALL INFILTRATIVE SHADOW IS PRESENT | 12(A3) | 10(B3) |
| INFILTRATIVE SHADOW IS ABSENT | 30(A4) | 10(B4) |

96

| TYPE | FIRST LIKELIHOOD RATIO LR1 |
|---|---|
| LARGE INFILTRATIVE SHADOW IS PRESENT | 0.07 |
| MEDIUM INFILTRATIVE SHADOW IS PRESENT | 0.6 |
| SMALL INFILTRATIVE SHADOW IS PRESENT | 1.92 |

WEIGHTING COEFFICIENT TABLE 97
(DISEASE NAME: INTERSTITIAL PNEUMONIA)

| TYPE | SIZE | FIRST WEIGHTING COEFFICIENT CF1 (FIRST PURPOSE) |
|---|---|---|
| INFILTRATIVE SHADOW | LARGE | 0.25 |
|  | MEDIUM | 0.5 |
|  | SMALL | 1.0 |

SIMILAR CASE SEARCH APPARATUS, METHOD FOR OPERATING SIMILAR CASE SEARCH APPARATUS, AND SIMILAR CASE SEARCH SYSTEM

CROSS-REFERENCE TO RELATED APPLICATIONS

This application is a Continuation of PCT International Application No. PCT/JP2017/041768 filed on 21 Nov. 2017, which claims priority under 35 U.S.C § 119(a) to Japanese Patent Application No. 2016-245304 filed on 19 Dec. 2016. The above application is hereby expressly incorporated by reference, in its entirety, into the present application.

BACKGROUND OF THE INVENTION

1. Field of the Invention

The present invention relates to a similar case search apparatus, a method for operating a similar case search apparatus, and a similar case search system.

2. Description of the Related Art

In the medical field, a similar case search has been performed which searches for a similar case including a case image similar to a target image as a medical examination target (also referred to as an interpretation target) from a plurality of cases including the case image (for example, see JP2015-191285A (corresponding to US2017/0011199A1)).

A similar case search apparatus disclosed in JP2015-191285A allows a doctor to designate a plurality of regions of interest, each of which includes one or more target lesions that are lesions present in a target image, and calculates feature amounts for each of the plurality of regions of interest. Then, the similar case search apparatus calculates an individual similarity which is a similarity between the region of interest and a case lesion that is a lesion present in the case image, on the basis of the feature amount of the region of interest and the feature amount of the case lesion and calculates a total similarity between the target image and the case image on the basis of the calculated individual similarity.

The second embodiment in JP2015-191285A discloses a technique that performs a weighting process of multiplying the individual similarity equal to or greater than a predetermined threshold value by a weighting coefficient in order to increase the total similarity of a case image having a case lesion similar to the region of interest to be higher than those of other case images. In addition, the fifth embodiment in JP2015-191285A discloses a technique that specifies the type of target lesion and the type of case lesion, for example, ground-glass opacity, an infiltrative shadow, and emphysema, and calculates only the individual similarity between the target lesion and the case lesion of the same type.

SUMMARY OF THE INVENTION

Similar cases are mainly referred to in a case in which a disease name is specified and a case in which the severity (also referred to as the degree of progression) of a disease is specified. In a case in which a disease name is specified, it is necessary to obtain an effective clue to specify a disease name from similar cases. For example, the commonality of the disease in a plurality of similar cases needs to be recognized. In a case in which the severity is specified, similarly, it is necessary to obtain an effective clue to specify the severity from similar cases. As such, the doctor wants the similar case that can give an effective clue corresponding to the reference purpose.

However, in the similar case search apparatus disclosed in JP2015-191285A, the similar case search is performed by focusing only on the type of lesion, that is, an image similarity that is the appearance of the lesion. For this reason, the similar case desired by the doctor may not be obtained depending on the purpose. Therefore, there is a room for improvement.

For example, an infiltrative shadow which is one of the types of lesions is a lesion that is seen in a case in which a medical condition has progressed, regardless of the type of disease. Therefore, the infiltrative shadow can be an effective clue to specify the severity, but is unlikely to be an effective clue to specify the disease name. In addition, since emphysema is a lesion that is commonly found in the lungs of the elderly, emphysema is unlikely to be an effective clue to specify the disease name, like the infiltrative shadow. That is, in the similar case search apparatus disclosed in JP2015-191285A, even in a case in which a similar case search is performed to specify a disease name and a plurality of similar cases in which the forms of infiltrative shadows or emphysema are visually similar are searched, the commonality of the disease may not be recognized in the plurality of similar cases. As a result, it is difficult to specify a disease name.

An object of the invention is to provide a similar case search apparatus, a method for operating a similar case search apparatus, and a similar case search system that can obtain a similar case desired by a doctor according to the purpose.

In order to achieve the object, according to the invention, there is provided a similar case search apparatus that searches for a similar case including a case image similar to a target image which is a medical examination target from a plurality of cases including the case image. The similar case search apparatus comprises: a first type acquisition unit that acquires a type of target lesion which is a lesion present in the target image; a second type acquisition unit that acquires a type of case lesion which is a lesion present in the case image; a first feature amount acquisition unit that acquires a feature amount of the target lesion; a second feature amount acquisition unit that acquires a feature amount of the case lesion; an individual lesion similarity calculation unit that calculates an individual lesion similarity which is a similarity between the target lesion and the case lesion of the same type on the basis of the feature amount of the target lesion and the feature amount of the case lesion; a weighting processing unit that performs a weighting process for the individual lesion similarity, using weighting coefficients which are preset for each of the types and a plurality of purposes; a total similarity calculation unit that calculates a total similarity between the target image and the case image for each of the purposes on the basis of the individual lesion similarity subjected to the weighting process; and a search unit that searches for the similar case on the basis of the total similarity.

Preferably, the weighting coefficients for the types and the purposes are set for each disease.

Preferably, the purposes include a purpose of specifying a disease name, and the weighting processing unit performs the weighting process, using a first weighting coefficient which is the weighting coefficient corresponding to a degree of contribution of each type to the specification of the disease name.

Preferably, the case includes the disease name, and the first weighting coefficient is set on the basis of a first likelihood ratio obtained by statistically analyzing a causal relationship between the case lesion and the disease name included in the case.

Preferably, the purposes include a purpose of specifying a severity of a disease, and the weighting processing unit performs the weighting process, using a second weighting coefficient which is the weighting coefficient corresponding to a degree of contribution of each type to the specification of the severity.

Preferably, the case includes the severity, and the second weighting coefficient is set on the basis of a second likelihood ratio obtained by statistically analyzing a causal relationship between the case lesion and the severity included in the case.

Preferably, the search unit creates a list of the searched similar cases for each of the purposes.

Preferably, the similar case search apparatus further comprises a screen output control unit that outputs a list display screen for displaying the list. The screen output control unit displays a first list which is the list corresponding to a first purpose and from which one of the similar cases is selected and displays a second list which is the list corresponding to a second purpose in a case in which one of the similar cases in the first list is selected on the list display screen. In this case, preferably, the first purpose is to specify a disease name and the second purpose is to specify the severity of a disease.

Preferably, the similar cases are arranged in the first list according to a candidate disease ranking which is a ranking of the disease names included in the similar cases on the basis of the total similarity corresponding to the first purpose, and the similar cases are arranged in the second list according to a ranking in the same disease which is a ranking of the total similarity corresponding to the second purpose in the similar cases of the same disease name.

According to the invention, there is provided a method for operating a similar case search apparatus that searches for a similar case including a case image similar to a target image which is a medical examination target from a plurality of cases including the case image. The method comprises: a first type acquisition step of acquiring a type of target lesion which is a lesion present in the target image; a second type acquisition step of acquiring a type of case lesion which is a lesion present in the case image; a first feature amount acquisition step of acquiring a feature amount of the target lesion; a second feature amount acquisition step of acquiring a feature amount of the case lesion; an individual lesion similarity calculation step of calculating an individual lesion similarity which is a similarity between the target lesion and the case lesion of the same type on the basis of the feature amount of the target lesion and the feature amount of the case lesion; a weighting processing step of performing a weighting process for the individual lesion similarity, using weighting coefficients which are preset for each of the types and a plurality of purposes; a total similarity calculation step of calculating a total similarity between the target image and the case image for each of the purposes on the basis of the individual lesion similarity subjected to the weighting process; and a search step of searching for the similar case on the basis of the total similarity.

According to the invention, there is provided a similar case search system including a similar case search apparatus that searches for a similar case including a case image similar to a target image which is a medical examination target from a plurality of cases including the case image and a client terminal that is connected to the similar case search apparatus by a network and is operated by a doctor. The similar case search system comprises: a first type acquisition unit that acquires a type of target lesion which is a lesion present in the target image; a second type acquisition unit that acquires a type of case lesion which is a lesion present in the case image; a first feature amount acquisition unit that acquires a feature amount of the target lesion; a second feature amount acquisition unit that acquires a feature amount of the case lesion; an individual lesion similarity calculation unit that calculates an individual lesion similarity which is a similarity between the target lesion and the case lesion of the same type on the basis of the feature amount of the target lesion and the feature amount of the case lesion; a weighting processing unit that performs a weighting process for the individual lesion similarity, using weighting coefficients which are preset for each of the types and a plurality of purposes; a total similarity calculation unit that calculates a total similarity between the target image and the case image for each of the purposes on the basis of the individual lesion similarity subjected to the weighting process; and a search unit that searches for the similar case on the basis of the total similarity.

According to the invention, the weighting process is performed for the individual lesion similarity which is the similarity between the target lesion and the case lesion of the same type, using the weighting coefficient considering the purpose of the similar case in addition to the type of lesion, that is, an image similarity. Therefore, it is possible to provide a similar case search apparatus, a method for operating a similar case search apparatus, and a similar case search system that can obtain a similar case desired by a doctor according to the purpose.

BRIEF DESCRIPTION OF THE DRAWINGS

FIG. 9 is a diagram illustrating the content of a weighting coefficient table.

FIG. 10 is a diagram illustrating the flow of a process of setting each weighting coefficient.

FIG. 11 is a diagram illustrating a method for setting a first weighting coefficient on the basis of a first likelihood ratio.

FIG. 12 is a diagram illustrating a method for setting a second t weighting coefficient on the basis of a second likelihood ratio.

FIG. 16 is a diagram illustrating similar cases.

FIG. 17 is a diagram illustrating a first list.

FIG. 18 is a diagram illustrating a second list.

FIG. 20 is a diagram illustrating a list display screen on which the second list is displayed.

FIG. 21 is a flowchart illustrating the processing procedure of the CPU in the similar case search server.

FIG. 22 is a diagram illustrating a first relational table and a weighting coefficient table in a case in which items are classified according to the size of a case lesion to increase the number of options.

DESCRIPTION OF THE PREFERRED EMBODIMENTS

Figure 1:
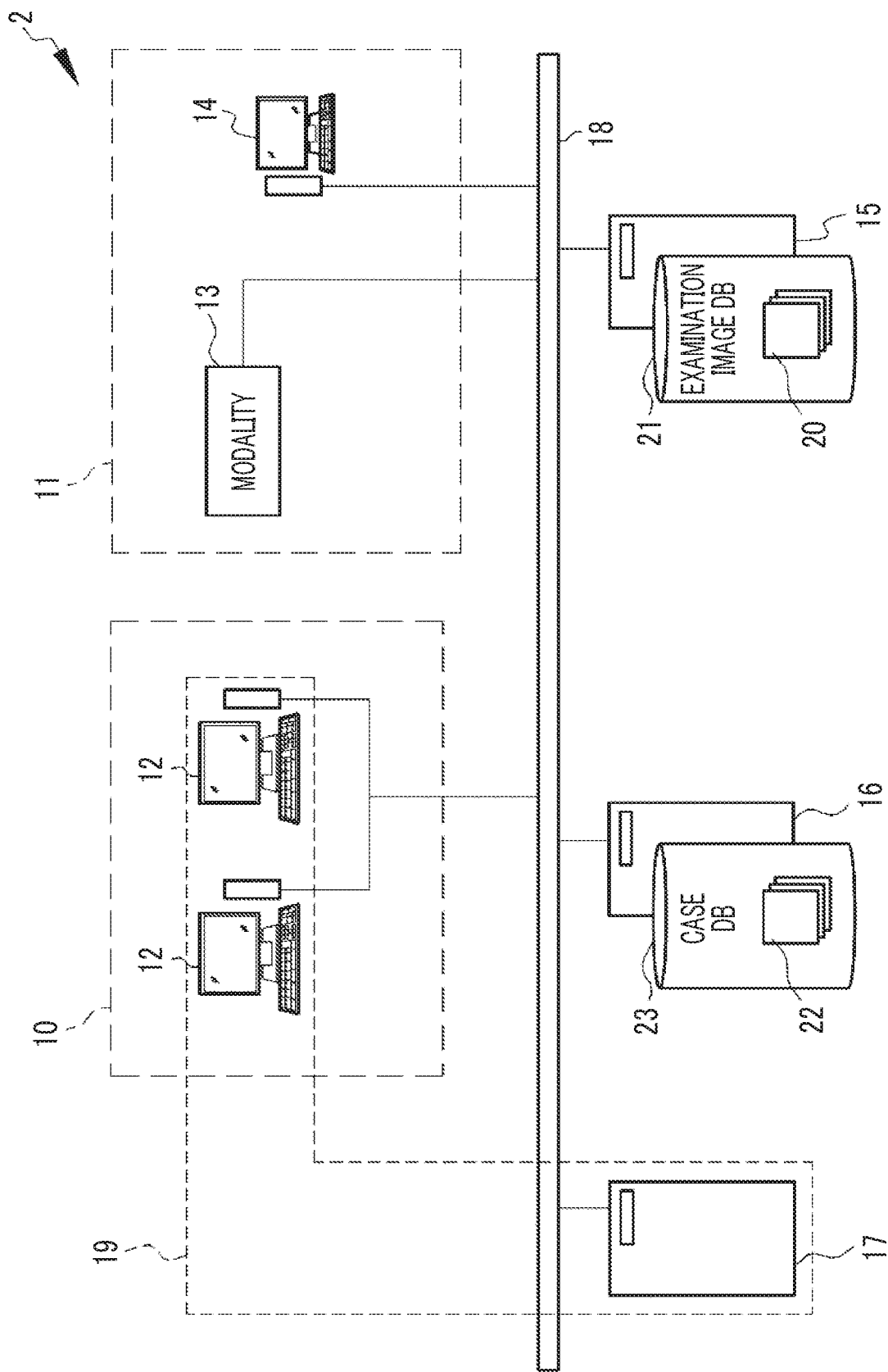
FIG. 1 is a diagram illustrating a medical information system including a similar case search server.

In FIG. 1, a medical information system 2 is constructed in a medical facility having a treatment department 10 or an examination department 11. The medical information system 2 includes a treatment department terminal 12 that corresponds to a client terminal and is provided in the treatment department 10, a modality 13 and an order management terminal 14 that are provided in the examination department 11, an examination image database (hereinafter, referred to as "DB") server 15, a case DB server 16, and a similar case search server 17 corresponding to a similar case search apparatus. These components are connected to each other through a network 18 such as a local area network (LAN) which is provided in the medical facility.

The treatment department terminal 12 forms the similar case search server 17 and a similar case search system 19. The treatment department terminal 12 is used by a doctor DR (see FIG. 3) in the treatment department 10 to input or browse electronic medical records and to issue an examination order to request various medical examinations to the examination department 11. In addition, the treatment department terminal 12 is used to browse examination images 20 captured by the modality 13 or similar cases (which will be described below) searched by the similar case search server 17.

The modality 13 is, for example, a computed tomography (CT) apparatus or a magnetic resonance imaging (MRI) apparatus that captures tomographic images as the examination images 20 or a plain X-ray imaging apparatus that captures plain X-ray images as the examination images 20. The order management terminal 14 receives the examination order issued by the treatment department terminal 12 and manages the received examination order. The examination order includes various items including order identification data (ID) for identifying an individual examination order, the ID of the treatment department terminal 12 or the doctor ID of the doctor DR that issues the examination order, the patient ID of a patient whose image is to be captured by the examination order, an examination purpose, such as follow-up observation, an imaging part such as the head or the chest, and a direction, such as a supine posture or a lying posture. A technician in the examination department 11 checks the content of the examination order with the order management terminal 14, sets imaging conditions corresponding to the checked examination order in the modality 13, and takes the examination image 20.

In a case in which the modality 13 captures the examination image 20, the technician inputs information, such as the patient ID of the patient who is an imaging target and the technician ID of the technician who takes charge of imaging. The input information is associated as accessory information with the examination image 20.

For example, the examination image 20 is created in a data file format based on the digital imaging and communications in medicine (DICOM) standard. The data file based on the DICOM standard is provided with a region for storing the body data of the examination image 20 and a region for storing the accessory information. The accessory information includes patient information, such as a patient ID, a patient name, and the sex, age, height, and weight of a patient, examination information, such as an order ID, a doctor ID, an examination date and time, an examination purpose, an imaging part, an imaging direction, imaging conditions, a technician ID, and the type of medical examination (the type of the modality 13 such as CT or MRI), and an image ID for identifying the individual examination image 20. The image ID is automatically assigned by the modality 13 in a case in which the examination image 20 is captured. The modality 13 transmits the examination image 20 to the examination image DB server 15.

Only one examination image 20 may be captured in response to one examination order as in a plane X-ray imaging apparatus or a plurality of examination images 20 may be captured in response to one examination order as in a CT apparatus or an MRI apparatus. In the latter case, an image ID (see FIG. 2) including numbers or symbols common to a plurality of examination images and a serial number is assigned and a plurality of examination images are handled as one set of examination images 20 captured in response to one examination order.

The examination image DB server 15 is a so-called picture archiving and communication system (PACS) server and includes an examination image DB 21 that stores a plurality of examination images 20 transmitted from the modality 13. The examination image DB server 15 transmits the examination image 20 to the treatment department terminal 12.

The case DB server 16 includes a case DB 23 that stores a plurality of cases 22. The case DB server 16 transmits the case 22 to the similar case search server 17.

Figure 2:
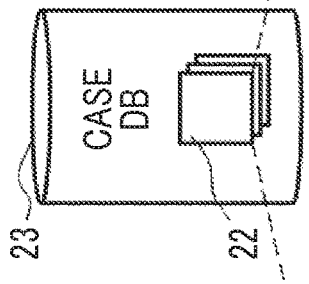
FIG. 2 is a diagram illustrating the content of a case.

In FIG. 2, the case DB server 16 assigns a case ID for identifying the individual case 22 to the case 22. The case 22 includes a case image 20C, case lesion information, a disease name, and severity. The case image 20C is the examination image 20 that was used for a medical examination in the past. In FIG. 2, one set of 20 tomographic images with image IDs "F001-1 to F001-20" captured by the CT apparatus is illustrated as the case images 20C.

The case lesion information is information related to a case lesion which is a lesion present in the case image 20C. The case lesion information includes a lesion ID for identifying each case lesion, the type of case lesion, and a feature amount ZC of a case lesion. FIG. 2 illustrates an example in which, for example, ground-glass opacity and an infiltrative shadow are registered as the types of case lesion, bacterial pneumonia is registered as a disease name, and a mild level is registered as severity.

The type of case lesion was specified by a lesion extraction unit 62 (see FIG. 7) of the similar case search server 17 at the time of the past medical examination. Similarly, the feature amount ZC of the case lesion was calculated by a feature amount calculation unit 63 (see FIG. 7) of the similar case search server 17 at the time of the past medical examination. The disease name and the severity were specified by the doctor DR at the time of the past medical examination.

Examples of the type of lesion include mass shadows, small nodular shadows, reticular shadows, linear shadows, punctate shadows, honeycomb lungs, cysts, emphysema, pneumothorax, bulla, cavity, bronchial wall thickening, bronchodilatation, traction bronchiectasis, air bronchogram, pleural thickening, and pleural effusion, in addition to the ground-glass opacity and the infiltrative shadow (see FIG. 9).

In FIG. 2, there are a plurality of types of feature amounts Z, as represented by ZC11, ZC21, ZC31, . . . . A multi-dimensional vector having the plurality of types of feature amounts Z as elements is referred to as a feature vector. The feature amounts Z include feature amounts related to the size of a lesion, such as the area of a lesion, the percentage of a lesion to the whole, the length of the major axis of a lesion, and the length of the minor axis of a lesion, feature amounts related to the position of a lesion, such as the distance of a lesion from other lesions, the distance from the chest wall, and the lung lobes, such as the upper lobe, the middle lobe, the lower lobe, S1, and S2, and feature amounts related to concentration, such as the mean value and standard deviation of the concentration (pixel value) of a lesion. The above is an example of the feature amounts common to each lesion regardless of the type of lesion. In some cases, feature amounts, such as the unevenness of the periphery of a lesion, a concentration gradient at the boundary between a lesion and a normal part, the degree of spiculas, such as the number of spiculas and the length of the spiculas, and the size of the cavity, are individually added according to the type of lesion. In addition, the number in the highest digit among the numbers attached to the feature amount ZC illustrated in FIG. 2 indicates the type of feature amount and the numbers after the highest digit are the same as the numbers in the lesion ID and indicate a lesion with a lesion ID related to the feature amount ZC. This holds for a feature amount ZT (see FIG. 7) of a target lesion which will be described below.

It goes without saying that there are many disease names in addition to the bacterial pneumonia illustrated in FIG. 2. The severity is divided into two levels, that is, a mild level and a severe level illustrated in FIG. 2. In the case of a disease, such as a cancer, whose severity is expressed by stages, such as stage 1 and stage 2, each stage corresponds to the mild level or the severe level.

Figure 3:
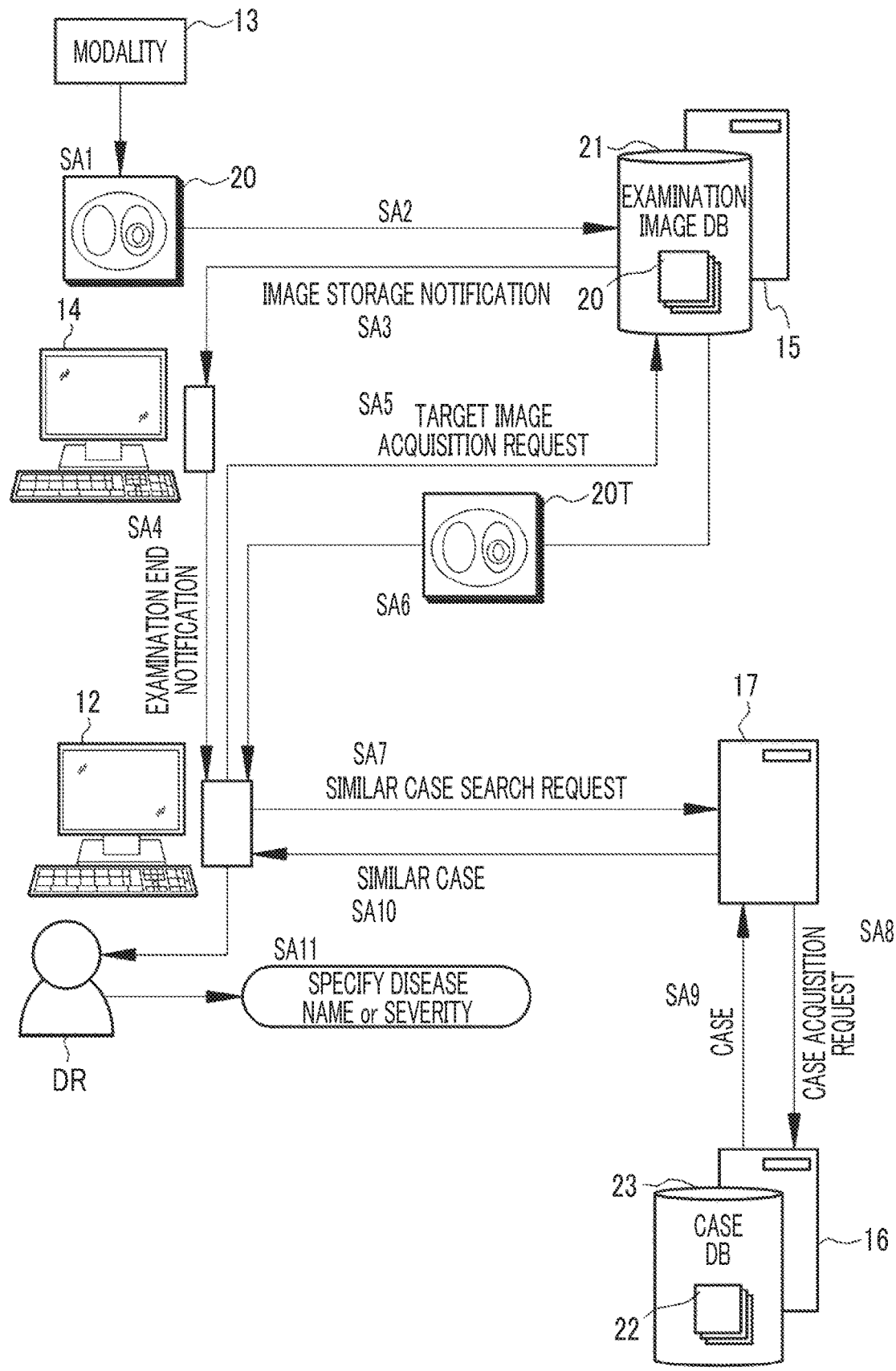
FIG. 3 is a diagram illustrating the flow of a process from an examination to the specification of a disease name or severity.

FIG. 3 illustrates the flow of a process from an examination to the specification of a disease name or the severity. First, the modality 13 performs imaging on the basis of an examination order and an examination image 20 is output from the modality 13 (Step SA1). The examination image 20 is transmitted from the modality 13 to the examination image DB server 15 and is stored in the examination image DB 21 by the examination image DB server 15 (Step SA2).

The examination image DB server 15 transmits an image storage notification indicating that the examination image 20 has been stored in the examination image DB 21 to the order management terminal 14 (Step SA3). In a case in which the image storage notification is received, the order management terminal 14 transmits an examination end notification to the treatment department terminal 12 that has issued the examination order (Step SA4). The image ID of the examination image 20 or the order ID is added to the image storage notification and the examination end notification.

The doctor DR checks the examination end notification through the treatment department terminal 12 and starts to examine the examination image 20 including the image ID or the order ID added to the examination end notification. Hereinafter, the examination image 20 to be examined is referred to as a target image 20T.

The doctor DR transmits a request to acquire the target image 20T to the examination image DB server 15 through the treatment department terminal 12 (Step SA5). The examination image DB server 15 receives the request to acquire the target image 20T and searches for the target image 20T corresponding to the request from the examination images 20 in the examination image DB 21. Then, the examination image DB server 15 transmits the searched target image 20T to the treatment department terminal 12 which has transmitted the acquisition request (Step SA6). The request to acquire the target image 20T includes various items of the accessory information of the examination image 20, for example, the order ID and the image ID. The examination image DB server 15 outputs an examination image 20 matched with the order ID and the image ID of the acquisition request as the target image 20T.

The doctor DR browses the target image 20T through the treatment department terminal 12. In a case in which the patient is suffering from any disease, there is a lesion (hereinafter, referred to as target lesion) showing symptoms of the disease in the target image 20T. In a case in which the doctor DR recognizes the target lesion, the doctor DR transmits a similar case search request to the similar case search server 17 through the treatment department terminal 12 in order to specify a disease name or the severity (Step SA7). The similar case is a case 22 including the case image 20C similar to the target image 20T.

The similar case search server 17 receives the similar case search request. The similar case search server 17 transmits a request to acquire the case 22 to the case DB server 16 (Step SA8). The case DB server 16 receives the request to acquire the case 22 and transmits all of the cases 22 in the case DB 23 to the similar case search server 17 (Step SA9). The similar case search server 17 searches for the case 22 including the case image 20C similar to the target image 20T, that is, a similar case from all of the cases 22. The similar case search server 17 transmits the searched similar case to the treatment department terminal 12 that has transmitted the search request (Step SA10).

The doctor DR browses the similar case through the treatment department terminal 12. The doctor DR specifies a disease name or the severity on the basis of, for example, the similar case and his or her own medical knowledge and experience (Step SA11). The doctor DR inputs the specified disease name or severity to an electronic medical record through the treatment department terminal 12.

As such, the doctor DR refers to the similar case for two purposes, that is, a purpose (hereinafter, referred to as a first purpose) of specifying a disease name and a purpose (hereinafter, referred to as a second purpose) of specifying the severity of a disease.

Figure 4:
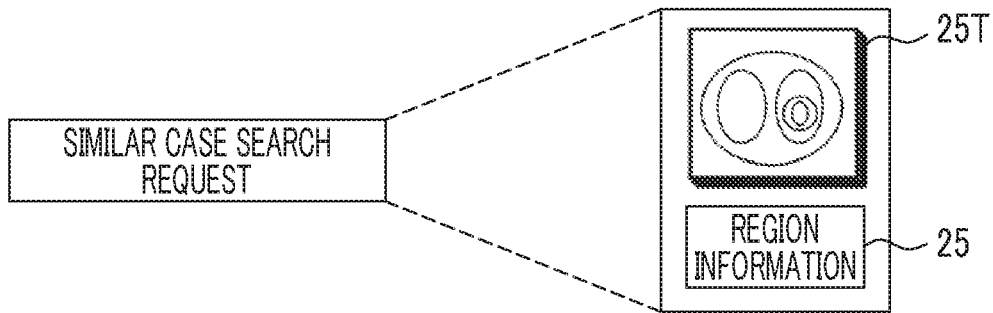
FIG. 4 is a diagram illustrating the content of a similar case search request.

In FIG. 4, the similar case search request transmitted from the treatment department terminal 12 to the similar case search server 17 includes the target image 20T and region information 25. The region information 25 is information of a region of interest (ROI, see FIG. 5) in the target image 20T which has been designated by the doctor DR through the treatment department terminal 12. The region information 25 is, for example, coordinate information in which the position of pixels forming the target image 20T is represented by two-dimensional or three-dimensional coordinates.

Figure 5:
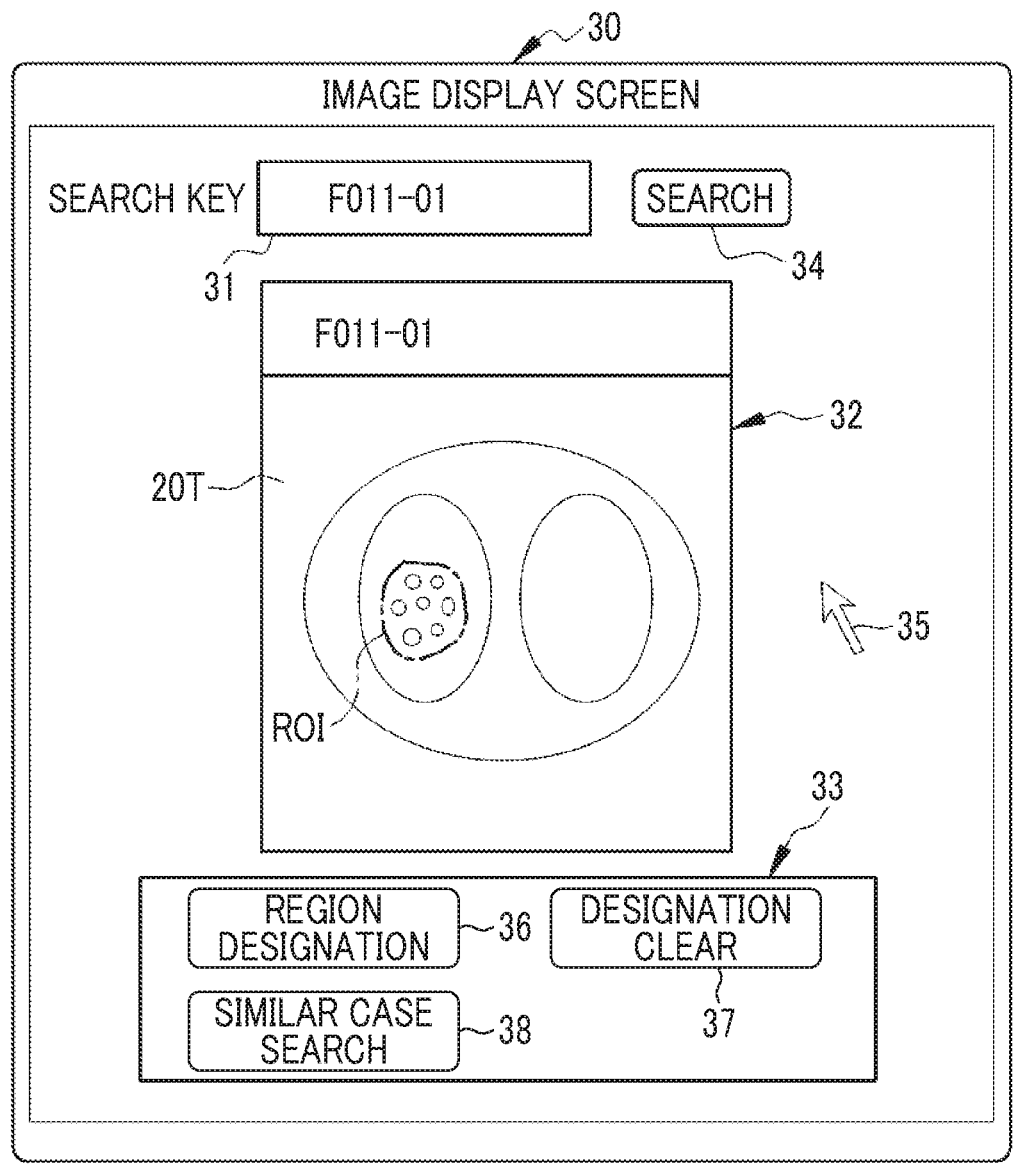
FIG. 5 is a diagram illustrating an image display screen on which a target image is displayed and which receives the designation of a region of interest.

The region of interest ROI is designated by an image display screen 30 illustrated in FIG. 5. The image display screen 30 is used by the doctor DR to browse the target image 20T from the examination image DB server 15 and is displayed on a display of the treatment department terminal 12.

The image display screen 30 is provided with, for example, an input box 31 for inputting the image ID and the order ID added to the examination end notification, an image display region 32 for displaying the target image 20T, and a button display region 33.

A search button 34 is provided beside the input box 31. In a case in which a desired image ID or order ID is input to the input box 31 and the search button 34 is selected by a cursor 35, a request to acquire the target image 20T is transmitted to the examination image DB server 15. The target image 20T corresponding to the acquisition request and the image ID of the target image 20T are displayed in the image display region 32. In a case in which a plurality of target images 20T form one set, the target images 20T displayed in the image display region 32 can be switched in the set by, for example, a scroll operation or a frame advance operation.

The button display region 33 is provided with a region designation button 36, a designation clear button 37, and a similar case search button 38. The region designation button 36 is an operation button for designating the region of interest ROI and the designation clear button 37 is an operation button for canceling the designated region of interest ROI. In a case in which the region designation button 36 is selected by the cursor 35, a region designation operation for designating any region of the target image 20T in the image display region 32 is available.

The region designation operation is performed by, for example, designating a plurality of control points with the cursor 35 such that the outer periphery of a region including a target lesion which has been visually recognized by the doctor DR in the target image 20T. The inside of a spline that draws a smooth curve indicated by a one-dot chain line passing through the plurality of control points is designated as the region of interest ROI. In a case in which there are a plurality of target lesions in the target image 20T, the doctor DR designates, as the region of interest ROI, a region including a representative lesion which is considered to be important for distinguishing the disease.

In a case in which the similar case search button 38 is selected by the cursor 35 after the region of interest ROI is designated by the spline, a similar case search request including the target image 20T displayed in the image display region 32 at that time and the information of the region of interest ROI designated by the spline, that is, the region information 25 is transmitted to the similar case search server 17. In addition, a plurality of regions of interest ROI can be designated for one target image 20T.

Figure 6:
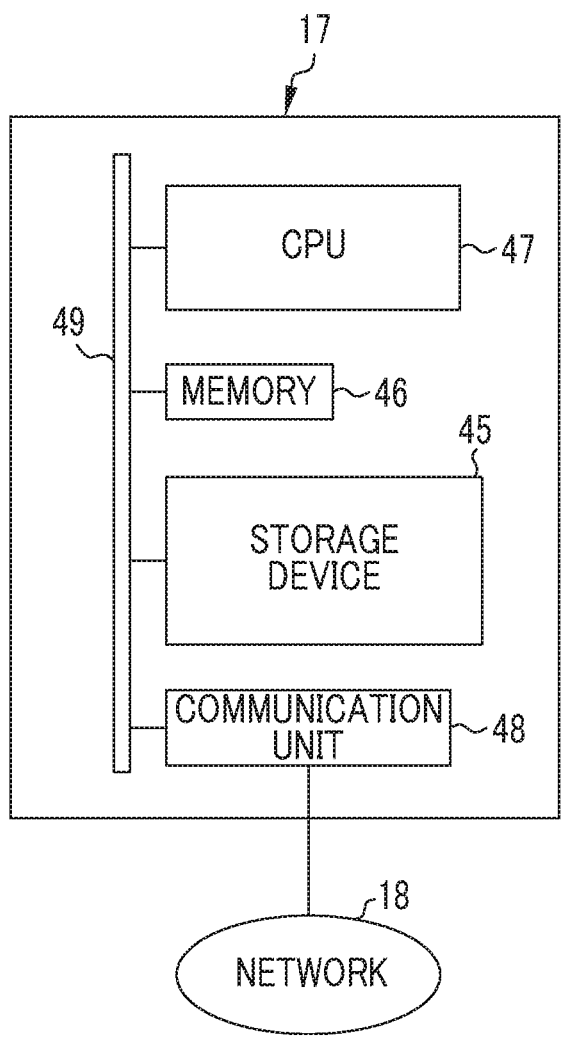
FIG. 6 is a block diagram illustrating a computer forming the similar case search server.

In FIG. 6, a computer forming the similar case search server 17 comprises a storage device 45, a memory 46, a central processing unit (CPU) 47, and a communication unit 48. These components are connected to each other through a data bus 49.

The storage device 45 is, for example, a hard disk drive that is provided in the computer forming the similar case search server 17 or is connected to the computer through a cable or a network or a disk array that is obtained by connecting a plurality of hard disk drives. The storage device 45 stores, for example, a control program, such as an operating system, various application programs (hereinafter, abbreviated to APs), and various types of data associated with these programs.

The memory 46 is a work memory that is used by the CPU 47 to perform processes. The CPU 47 loads the program stored in the storage device 45 to the memory 46 and performs a process based on the program to control the overall operation of each unit of the computer.

The communication unit 48 is a network interface that controls the transmission of various kinds of information to, for example, the treatment department terminal 12 through the network 18. The communication unit 48 receives the case 22 from the case DB server 16, receives the similar case search request from the treatment department terminal 12, transmits the request to acquire the case 22 to the case DB server 16, and transmits similar cases to the treatment department terminal 12.

Figure 7:
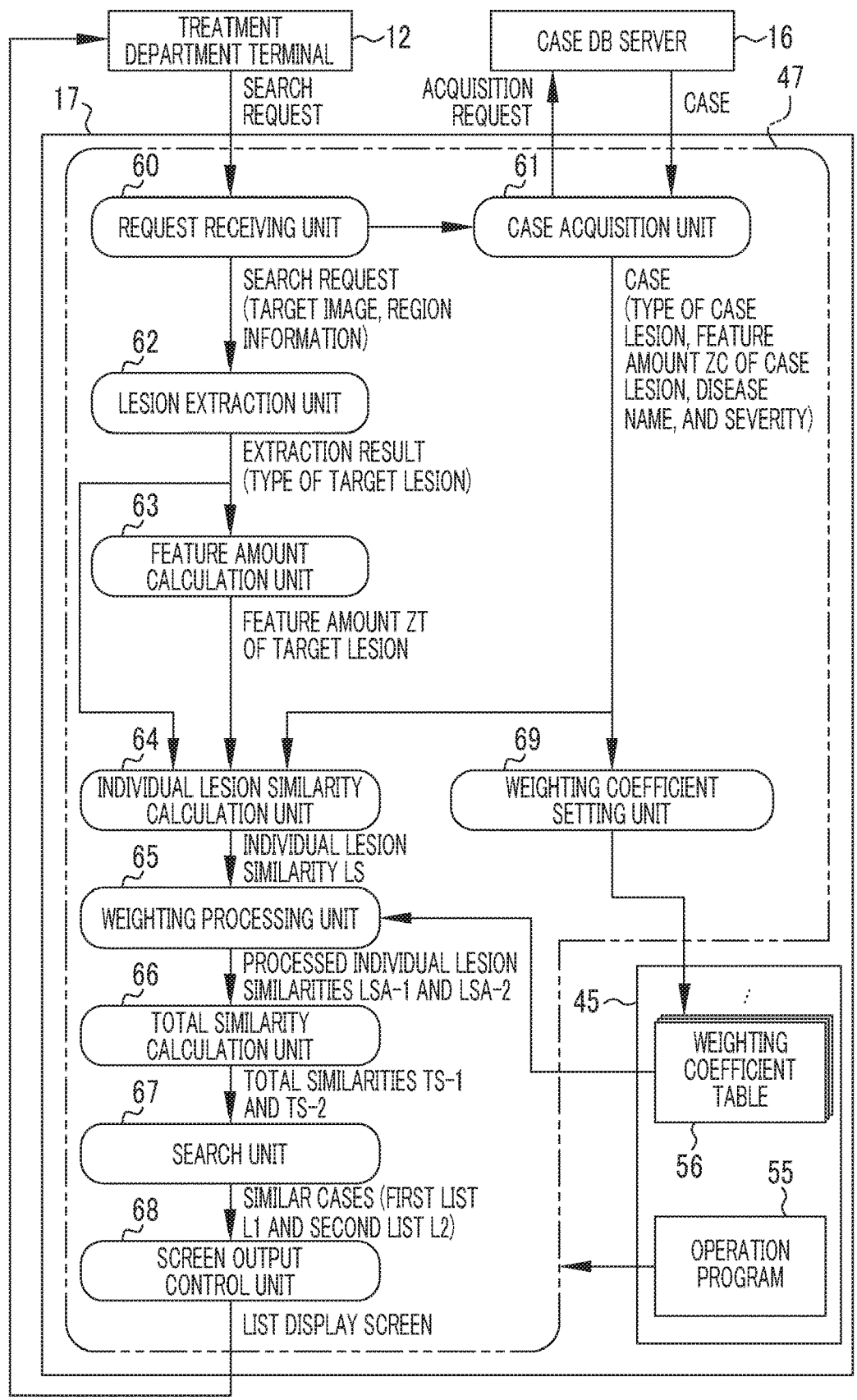
FIG. 7 is a block diagram illustrating the functions of a CPU in the similar case search server.

In FIG. 7, an operation program 55 is stored as the AP in the storage device 45 of the similar case search server 17. The operation program 55 is an AP that causes the computer forming the similar case search server 17 to function as a similar case search apparatus. The storage device 45 stores a weighting coefficient table 56 (see FIG. 9) in addition to the operation program 55.

In a case in which the operation program 55 runs, the CPU 47 of the similar case search server 17 functions as a request receiving unit 60, a case acquisition unit 61, a lesion extraction unit 62, a feature amount calculation unit 63, an individual lesion similarity calculation unit 64, a weighting processing unit 65, a total similarity calculation unit 66, a search unit 67, a screen output control unit 68, and a weighting coefficient setting unit 69 in cooperation with, for example, the memory 46.

The request receiving unit 60 receives the similar case search request from the treatment department terminal 12. The request receiving unit 60 outputs a notification indicating that the similar case search request has been received to the case acquisition unit 61. In addition, the request receiving unit 60 outputs the similar case search request to the lesion extraction unit 62.

In a case in which the notification indicating that the similar case search request has been received is received from the request receiving unit 60, the case acquisition unit 61 outputs a request to acquire the case 22 the case DB server 16. Then, the case acquisition unit 61 acquires the case 22 transmitted from the case DB server 16 in response to the acquisition request. The case acquisition unit 61 outputs the case 22 to the individual lesion similarity calculation unit 64 and the weighting coefficient setting unit 69.

As illustrated in FIG. 2, the type of case lesion and the feature amount ZC of the case lesion are registered as case lesion information in the case 22. That is, the case acquisition unit 61 that acquires the case 22 corresponds to a second type acquisition unit that acquires the type of case lesion and a second feature amount acquisition unit that acquires the feature amount ZC of the case lesion and has a second type acquisition function and a second feature amount acquisition function.

The lesion extraction unit 62 performs image analysis for the region of interest ROI indicated by the region information 25 included in the similar case search request to extract a target lesion in the region of interest ROI. The lesion extraction unit 62 specifies the type of target lesion in the process of extracting the target lesion. That is, the lesion extraction unit 62 corresponds to a first type acquisition unit that acquires the type of target lesion and has a first type acquisition function.

First, the lesion extraction unit 62 divides the region of interest ROI into a plurality of small regions, for example, square regions corresponding to the number of pixels. Then, the lesion extraction unit 62 calculates feature amounts related to the concentration of each of the divided small regions, for example, the mean value, maximum value, minimum value, mode, and standard deviation of the concentration.

Then, the lesion extraction unit 62 specifies the type of lesion to which each small region belongs, on the basis of the calculated feature amounts. A machine learning algorithm, such as Adaptive Boosting (AdaBoost) or Deep Learning, is used to specify the type of lesion. That is, a plurality of sets of the lesions whose types have been determined and the feature amounts of the lesions or a plurality of examination images 20 are input as sample data, the relationship between the type and the feature amounts is learned, and the type corresponding to the calculated feature amounts is returned.

Finally, a group of small regions specified as the same type is extracted as one target lesion. The lesion extraction unit 62 assigns a lesion ID to the extracted target lesion, associates the coordinate information of the extracted target lesion and the specified type with the lesion ID, and outputs the associated data as the extraction result to the feature amount calculation unit 63 and the individual lesion similarity calculation unit 64.

The feature amount calculation unit 63 calculates the feature amount ZT of the target lesion. That is, the feature amount calculation unit 63 corresponds to a first feature amount acquisition unit that acquires the feature amount ZT of the target lesion and has a first feature amount acquisition function. In a case in which there are a plurality of target lesions, the feature amount calculation unit 63 calculates the feature amount ZT of each of the plurality of target lesions. The feature amount calculation unit 63 outputs the calculated feature amount ZT of the target lesion to the individual lesion similarity calculation unit 64.

The individual lesion similarity calculation unit 64 has an individual lesion similarity calculation function of calculating an individual lesion similarity LS which is a similarity between the target lesion and the case lesion of the same type. The individual lesion similarity calculation unit 64 outputs the calculated individual lesion similarity LS to the weighting processing unit 65.

The weighting processing unit 65 has a weighting processing function of performing a weighting process for the individual lesion similarity LS. The weighting processing unit 65 performs the weighting process using a first weighting coefficient CF1 (see FIG. 9) corresponding to the first purpose and a second weighting coefficient CF2 (see FIG. 9) corresponding to the second purpose. The weighting coefficients CF1 and CF2 have been registered in the weighting coefficient table 56. The weighting processing unit 65 outputs the individual lesion similarity subjected to the weighting process (hereinafter, referred to as a processed individual lesion similarity) to the total similarity calculation unit 66. Hereinafter, the processed individual lesion similarity subjected to the weighting process using the first weighting coefficient CF1 corresponding to the first purpose is represented by a processed individual lesion similarity LSA-1 and the processed individual lesion similarity subjected to the weighting process using the second weighting coefficient CF2 corresponding to the second purpose is represented by a processed individual lesion similarity LSA-2.

The total similarity calculation unit 66 has a total similarity calculation function of calculating a total similarity between the target image 20T and the case image 20C for each of the first purpose and the second purpose on the basis of the processed individual lesion similarities LSA-1 and LSA-2. Hereinafter, the total similarity which corresponds to the first purpose and has been calculated on the basis of the processed individual lesion similarity LSA-1 is represented by a total similarity TS-1 and the total similarity which corresponds to the second purpose and has been calculated on the basis of the processed individual lesion similarity LSA-2 is represented by a total similarity TS-2. The total similarity calculation unit 66 outputs the calculated total similarities TS-1 and TS-2 to the search unit 67.

The search unit 67 has a search function of searching for similar cases on the basis of the total similarities TS-1 and TS-2. The search unit 67 creates a list of the searched similar cases for each purpose. Hereinafter, the list corresponding to the first purpose is represented by a first list L1 (see FIG. 17 and FIG. 19) and the list corresponding to the second purpose is represented by a second list L2 (see FIG. 18 and FIG. 20). The search unit 67 outputs the created first and second lists to the screen output control unit 68.

The screen output control unit 68 has a screen output control function of outputting a list display screen 85 (see FIG. 19 and FIG. 20) for displaying the first list L1 and the second list L2 to the treatment department terminal 12. The screen output control unit 68 outputs various screens including the image display screen 30 illustrated in FIG. 5 to the treatment department terminal 12 in addition to the list display screen 85.

The screen output control unit 68 outputs various screens including the image display screen 30 and the list display screen 85 in the form of screen data for web distribution created by a markup language, such as an extensible markup language (XML). Then, it is possible to browse various screens on the web browser through the treatment department terminal 12. Other languages, such as JavaScript (registered trademark) Object Notation (JSON), may be used instead of XML.

Figure 8:
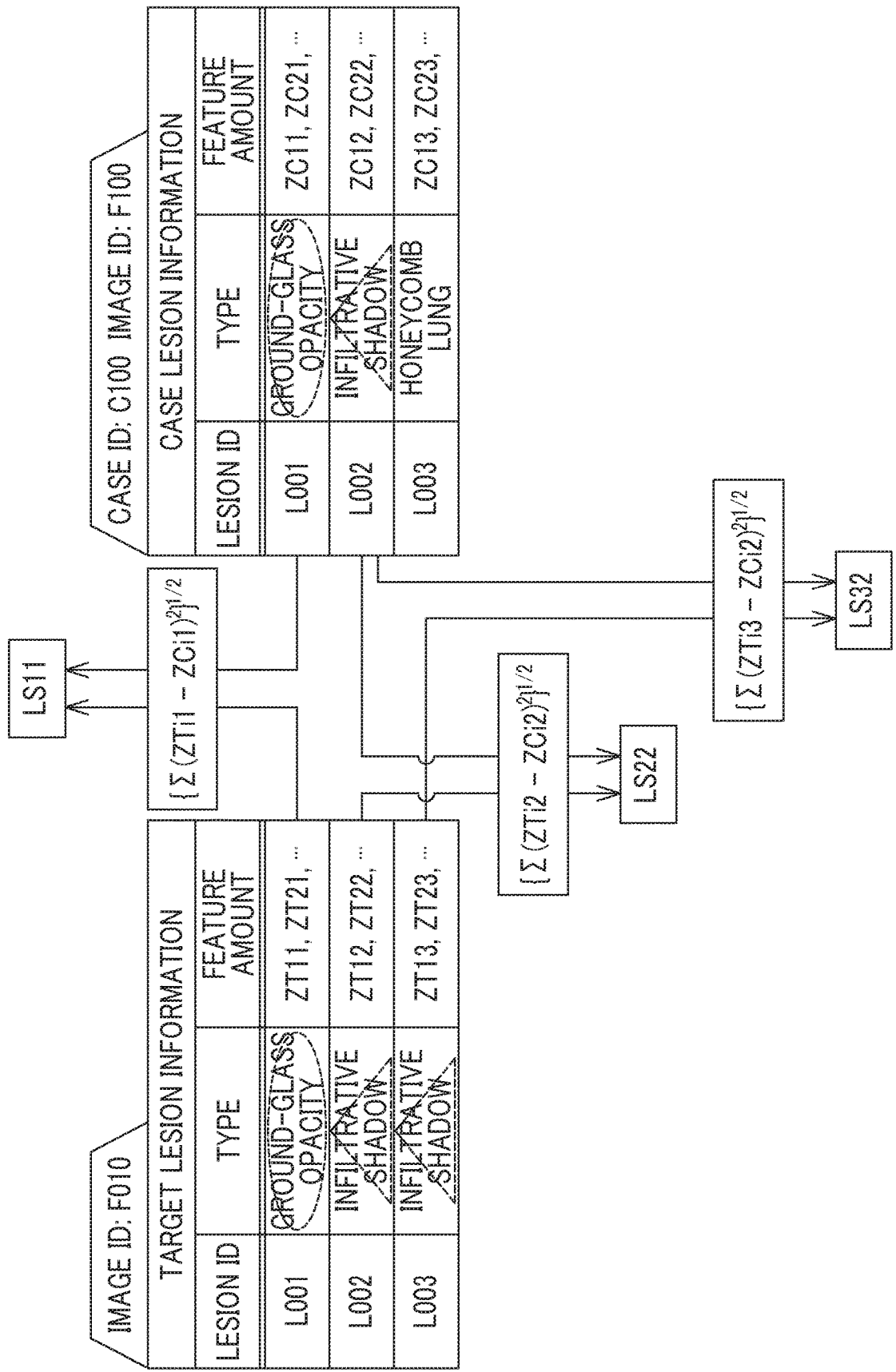
FIG. 8 is a diagram illustrating an individual lesion similarity calculation method.

In FIG. 8, the lesion ID and type of the target lesion extracted by the lesion extraction unit 62 and the feature amount ZT of the target lesion calculated by the feature amount calculation unit 63 are information that forms a pair with the case lesion information of the case 22 and are hereinafter referred to as target lesion information.

The individual lesion similarity calculation unit 64 compares the type items of the target lesion information and the case lesion information to specify the target lesion and the case lesion which are the same type. Then, the individual lesion similarity calculation unit 64 calculates the individual lesion similarity LS on the basis of the feature amounts ZT and ZC of the target lesion and the case lesion which are the same type.

Specifically, the individual lesion similarity calculation unit 64 calculates, as the individual lesion similarity LS, the square root of the sum of the squares of the differences (ZTi−ZCi) between a plurality of types of feature amounts ZTi (i is the type of feature amount) of the target lesion and a plurality of types of feature amounts ZCi of the case lesion, that is, a distance between a feature vector having the feature amount ZTi as an element and a feature vector having the feature amount ZCi as an element. In this case, the similarity between the target lesion and the case lesion becomes higher as the value of the individual lesion similarity LS becomes smaller (the distance between the feature vector having the feature amount ZTi as an element and the feature vector having the feature amount ZCi as an element becomes shorter). In addition, the feature amounts ZTi and ZCi are normalized before the calculation of the individual lesion similarity LS and the values of the feature amounts ZTi and ZCi are adjusted if necessary. For example, the square of the difference (ZTi−ZCi) is multiplied by an appropriate coefficient Wi.

In a case in which there are a plurality of sets of the target lesions and the case lesions which are the same type, the individual lesion similarity calculation unit 64 calculates the individual lesion similarity LS for each of the plurality of sets. The individual lesion similarity calculation unit 64 calculates the individual lesion similarity LS for all of the cases 22. In addition, in a case in which there are no target lesion and case lesions of the same type, the individual lesion similarity calculation unit 64 does not calculate the individual lesion similarity LS and the case 22 is excluded from the similar case candidates. Alternatively, the individual lesion similarity LS may be calculated using the default value of the feature amount Z (for example, the area of the lesion=0) in a case in which there are no target lesions and case lesions of the same type. Next, an example of the former case in which the case 22 without a case lesion that is the same type as the target lesion is excluded from the similar case candidates will be described.

FIG. 8 illustrates the target lesion information of a target image 20T with an image ID "F010" and the case lesion information of a case image 20C with an image ID "F100" in a case 22 with a case ID "C100". A target lesion with a lesion ID "L001" and a case lesion with a lesion ID "L001" are the same ground-glass opacity, a target lesion with a lesion ID "L002" and a case lesion with a lesion ID "L002" are the same infiltrative shadow, and a target lesion with a lesion ID "L003" and the case lesion with the lesion ID "L002" are the same infiltrative shadow. That is, there are a total of three sets of the target lesions and the case lesions which are the same type.

In this case, the individual lesion similarity calculation unit 64 calculates an individual lesion similarity LS11 between the target lesion with the lesion ID "L001" and the case lesion with the lesion ID "L001", an individual lesion similarity LS22 between the target lesion with the lesion ID "L002" and the case lesion with the lesion ID "L002", and an individual lesion similarity LS32 between the target lesion with the lesion ID "L003" and the case lesion with the lesion ID "L002". The individual lesion similarity LS between the target lesion and the case lesion of different types are not calculated. For example, the individual lesion similarity LS between the target lesion with the lesion ID "L001" which is the ground-glass opacity and the case lesion with the lesion ID "L003" which is the honeycomb lung is not calculated.

The individual lesion similarity calculation unit 64 calculates each of the individual lesion similarities LS11, LS22, and LS32 using the following expressions.

$$LS11=\{\Sigma(ZTi1-ZCi1)^2\}^{1/2}$$

$$LS22=\{\Sigma(ZTi2-ZCi2)^2\}^{1/2}$$

$$LS32=\{\Sigma(ZTi3-ZCi2)^2\}^{1/2}$$

As illustrated in FIG. 9, the weighting coefficient table 56 is provided for each disease, such as interstitial pneumonia, bacterial pneumonia, and hypersensitive pneumonia. The weighting coefficients include the first weighting coefficient CF1 and the second weighting coefficient CF2. Each of the weighting coefficients CF1 and CF2 is provided for each type of lesion. That is, for each disease, the weighting coefficients are set for each type of lesion and for each purpose.

The first weighting coefficient CF1 is a weighting coefficient for the first purpose of specifying a disease name. A value corresponding to the degree of contribution of each type of lesion to the specification of the disease name is set as the first weighting coefficient CF1. The second weighting factor CF2 is a weighting coefficient for the second purpose of specifying the severity. A value corresponding to the degree of contribution of each type of lesion to the specification of the severity is set as the second weighting factor CF2.

FIG. 9 illustrates an example of the weighting coefficient table 56 for the interstitial pneumonia. According to this table, the first weighting coefficient CF1 is 1.0 for the mass shadow and the nodular shadow, is 1.5 for the ground-glass opacity, the reticular shadow, and the honeycomb lung, is 0.5 for the linear shadow and the cyst, and is 0.25 for the infiltrative shadow and the emphysema. In this case, the ground-glass opacity, the reticular shadow, and the honeycomb lung having a relatively high first weighting coefficient CF1 of 1.5 are the types of lesions having a relatively high degree of contribution to the specification of the disease name of interstitial pneumonia and the infiltrative shadow and the emphysema having a relatively low first weighting coefficient CF1 of 0.25 are the types of lesions having a relatively low degree of contribution to the specification of the disease name of interstitial pneumonia.

In contrast, the second weighting coefficient CF2 is 1.0 for the nodular shadow, the linear shadow, the cyst, and the emphysema, is 2.0 for the infiltrative shadow, the mass shadow, and the honeycomb lung, and is 1.5 for the ground-glass opacity and the reticular shadow. In this case, the infiltrative shadow, the mass shadow, and the honeycomb lung having a relatively high second weighting coefficient CF2 of 2.0 are the types of lesions having a relatively high degree of contribution to the specification of the severity of interstitial pneumonia and the nodular shadow, the linear shadow, the cyst, and the emphysema having a relatively low second weighting coefficient CF2 of 1.0 are the types of lesions having a relatively low degree of contribution to the specification of the severity of interstitial pneumonia.

For the infiltrative shadow, the first weighting coefficient CF1 is 0.25 and the second weighting coefficient CF2 is 2.0 that is eight times the first weighting coefficient CF1. This is related to the fact that, since the infiltrative shadow is a lesion that is seen in a case in which a medical condition progresses, regardless of the type of disease, the infiltrative shadow can be an effective clue to specify the severity, but is not an effective clue to specify the disease name. Similarly, for emphysema, the first weighting coefficient CF1 is 0.25 and the second weighting coefficient CF2 is 1.0 that is four times the first weighting coefficient CF1. This is related to the fact that, since emphysema is a lesion generally found in the lungs of the elderly, emphysema is not an effective clue to specify the disease name.

As such, the first weighting coefficient CF1 is a weighting coefficient suitable for the first purpose of specifying the disease name and the second weighting coefficient CF2 is a weighting coefficient suitable for the second purpose of specifying the severity.

The weighting coefficient setting unit 69 sets the weighting coefficients on the basis of the case 22. Specifically, as illustrated in FIG. 10, the weighting coefficient setting unit 69 creates a first relational table 75A (see FIG. 11) indicating a causal relationship between the disease name and the case lesion of the case 22 on the basis of the case 22 (Step SB10). Then, the weighting coefficient setting unit 69 calculates a first likelihood ratio LR1 on the basis of the first relational table 75A (Step SB11) and sets the first weighting coefficient CF1 on the basis of the first likelihood ratio LR1 (Step SB12). In addition, the weighting coefficient setting unit 69 creates a second relational table 75B (see FIG. 12) indicating a causal relationship between the severity and the case lesion of the case 22 on the basis of the case 22 (Step SC10). Then, the weighting coefficient setting unit 69 calculates a second likelihood ratio LR2 on the basis of the second relational table 75B (Step SC11) and sets the second weighting coefficient CF2 on the basis of the second likelihood ratio LR2 (Step SC12).

As illustrated in FIG. 11, the first relational table 75A shows the statistics of the number of cases 22 of a specific disease and the number of cases 22 of diseases other than the specific disease in a case in which a specific type of case lesion is present and a case in which a specific type of case lesion is absent. The weighting coefficient setting unit 69 creates the first relational table 75A for each type of case lesion for each disease name registered in the cases 22. For example, in a case in which there are 100 types of disease names registered in the cases 22 and there are 20 types of case lesions, the weighting coefficient setting unit 69 creates 2000 (=100×20) first relational tables 75A.

It is assumed that the number of cases 22 of a specific disease in a case in which a specific type of case lesion is present is A1, the number of cases 22 of a specific disease in a case in which a specific type of case lesion is absent is A2, the number of cases 22 other than a specific disease in a case in which a specific type of case lesion is present is B1, and the number of cases 22 other than a specific disease in a case in which a specific type of case lesion is absent is B2. In this case, the first likelihood ratio LR1 is calculated by the following expression.

$$LR1=\{A1/(A1+A2)\}/\{B1/(B1+B2)\}$$

The weighting coefficient setting unit 69 calculates the first likelihood ratio LR1 for each first relational table 75A.

The first likelihood ratio LR1 is an index indicating the possibility of the patient suffering from a specific disease due to a specific type of lesion in a case in which the specific type of lesion is present, that is, an index indicating the likelihood of a specific disease in a case in which the specific type of lesion is absent.

The weighting coefficient setting unit 69 substitutes the calculated first likelihood ratio LR1 with the first weighting coefficient CF1 using a substitution table 76. Then, the weighting coefficient setting unit 69 registers the substituted first weighting coefficient CF1 in the weighting coefficient table 56.

Here, as the value of the likelihood ratio LR becomes larger, the likelihood of a specific disease in a case in which the specific type of lesion is present becomes higher. For example, in a case in which the likelihood ratio LR is greater than 5, a specific type of lesion can be an effective clue to specify a specific disease. In contrast, in a case in which the likelihood ratio LR is equal to or less than 0.5, a specific type of lesion is less likely to be an effective clue to specify a specific disease.

The substitution table 76 is prepared in advance on the basis of the above-mentioned characteristics of the likelihood ratio LR and is stored in the storage device 45 like the weighting coefficient table 56. The range of the value of the likelihood ratio LR and a weighting coefficient corresponding to the likelihood ratio LR are registered in the substitution table 76. In a case in which the likelihood ratio LR is equal to or less than 0.5 (LR≤0.5), the weighting coefficient is 0.25. In a case in which the likelihood ratio LR is greater than 0.5 and equal to or less than 1 (0.5<LR≤1), the weighting coefficient is 0.5. In a case in which the likelihood ratio LR is greater than 1 and equal to or less than 2 (1<LR≤2), the weighting coefficient is 1.0. In a case in which the likelihood ratio LR is greater than 2 and equal to or less than 5 (2<LR≤5), the weighting coefficient is 1.5. In a case in which the likelihood ratio LR is greater than 5 (5<LR), the weighting coefficient is 2.0.

FIG. 11 illustrates a case in which the type of lesion is an infiltrative shadow and the disease name is interstitial pneumonia. The following are registered in the first relational table 75A: the number A1 of cases 22 of interstitial pneumonia in a case in which an infiltrative shadow is present is 20; the number A2 of cases 22 of interstitial pneumonia in a case in which an infiltrative shadow is absent is 30; the number B1 of cases 22 of diseases other than interstitial pneumonia in a case in which an infiltrative shadow is present is 70; and the number B2 of cases 22 of diseases other than interstitial pneumonia in a case in which an infiltrative shadow is absent is 10. In this case, the first likelihood ratio LR1 is as follows.

$$LR1=\{20/(20+30)\}/\{70/(70+10)\}\approx 0.46$$

According to the substitution table 76, 0.46 corresponds to LR≤0.5 and a weighting coefficient corresponding to the value is 0.25. Therefore, in this case, 0.25 is set as the first weighting coefficient CF1. In addition, SB10 to SB12 in FIG. 11 correspond to Steps SB10 to SB12 illustrated in FIG. 10, respectively.

As illustrated in FIG. 12, the second relational table 75B shows the statistics of the number of cases 22 in which a specific disease is a severe disease and the number of cases 22 in which a specific disease is not a severe disease in a case in which a specific type of case lesion is present and a case in which a specific type of case lesion is absent. In the second relational table 75B, the target is narrowed only to the cases 22 of a specific disease unlike the first relational table 75A in which the target is the cases 22 of diseases other than a specific disease. As in the first relational table 75A, the weighting coefficient setting unit 69 creates the second relational table 75B for each type of case lesion for each disease name registered in the cases 22.

It is assumed that the number of cases 22 in which a specific disease is a severe disease in a case in which a specific type of case lesion is present is C1, the number of cases 22 in which a specific disease is a severe disease in a case in which a specific type of case lesion is absent is C2, the number of cases 22 in which a specific disease is not a severe disease in a case in which a specific type of case lesion is present is D1, and the number of cases 22 in which a specific disease is not a severe disease in a case in which a specific type of case lesion is absent is D2. In this case, the second likelihood ratio LR2 is calculated by the following expression.

$$LR2=\{C1/(C1+C2)\}/\{D1/(D1+D2)\}$$

The weighting coefficient setting unit 69 calculates the second likelihood ratio LR2 for each second relational table 75B.

In addition, A1 of the first relational table 75A and C1 and D1 of the second relational table 75B which have the same disease name and are the same type satisfy the following relationship: A1=C1+D1, which is natural in terms of the properties of the first relational table 75A and the second relational table 75B.

In addition, A2 of the first relational table 75A and C2 and D2 of the second relational table 75B which have the same disease name and are the same type satisfy the following relationship: A2=C2+D2.

The second likelihood ratio LR2 is an index indicating the possibility of a specific disease being a severe disease due to a specific type of lesion in a case in which the specific type of lesion is present, that is, an index indicating the likelihood of a specific disease being a severe disease in a case in which a specific type of lesion is present.

The weighting coefficient setting unit 69 substitutes the calculated second likelihood ratio LR2 with the second weighting coefficient CF2 using the substitution table 76 as in the first likelihood ratio LR1. Then, the weighting coefficient setting unit 69 registers the substituted second weighting coefficient CF2 in the weighting coefficient table 56.

FIG. 12 illustrates a case in which the type of lesion is an infiltrative shadow and the disease name is interstitial pneumonia, as in FIG. 11. The following are registered in the second relational table 75B: the number C1 of cases 22 of severe interstitial pneumonia in a case in which an infiltrative shadow is present is 15; the number C2 of cases 22 of severe interstitial pneumonia in a case in which an infiltrative shadow is absent is 3; the number D1 of cases 22 of interstitial pneumonia that is not sever in a case in which an infiltrative shadow is present 5; and the number D2 of cases 22 of interstitial pneumonia that is not sever in a case in which an infiltrative shadow is absent is 27: In this case, the second likelihood ratio LR2 is as follows: $LR2=\{15/(15+3)\}/\{5/(5+27)\}\approx 5.33$. According to the substitution table 76, 5.33 corresponds to 5<LR and a weighting coefficient corresponding to the value is 2.0. Therefore, in this case, 2.0 is set as the second weighting coefficient CF2. Similarly to FIG. 11, SC10 to SC12 in FIG. 12 correspond to Steps SC10 to SC12 illustrated in FIG. 10, respectively.

The weighting coefficient setting unit 69 receives the case 22 from the case acquisition unit 61 periodically, for example, every month and sets the weighting coefficients CF1 and CF2. Therefore, the value of each of the weighting coefficients CF1 and CF2 is likely to change over time. Of course, each of the weighting coefficients CF1 and CF2 may be a fixed value. In this case, the cases are not limited to the cases 22 of one medical facility and each of the weighting coefficients CF1 and CF2 is set on the basis of, for example, the cases of a plurality of medical facilities connected by regional medical cooperation. Each of the weighting coefficients CF1 and CF2 with the fixed values may be used in a case in which the number of cases 22 is less than a predetermined value. Each of the weighting coefficients CF1 and CF2 may be set periodically in a case in which the number of cases 22 is equal to the predetermined value.

Figure 13:
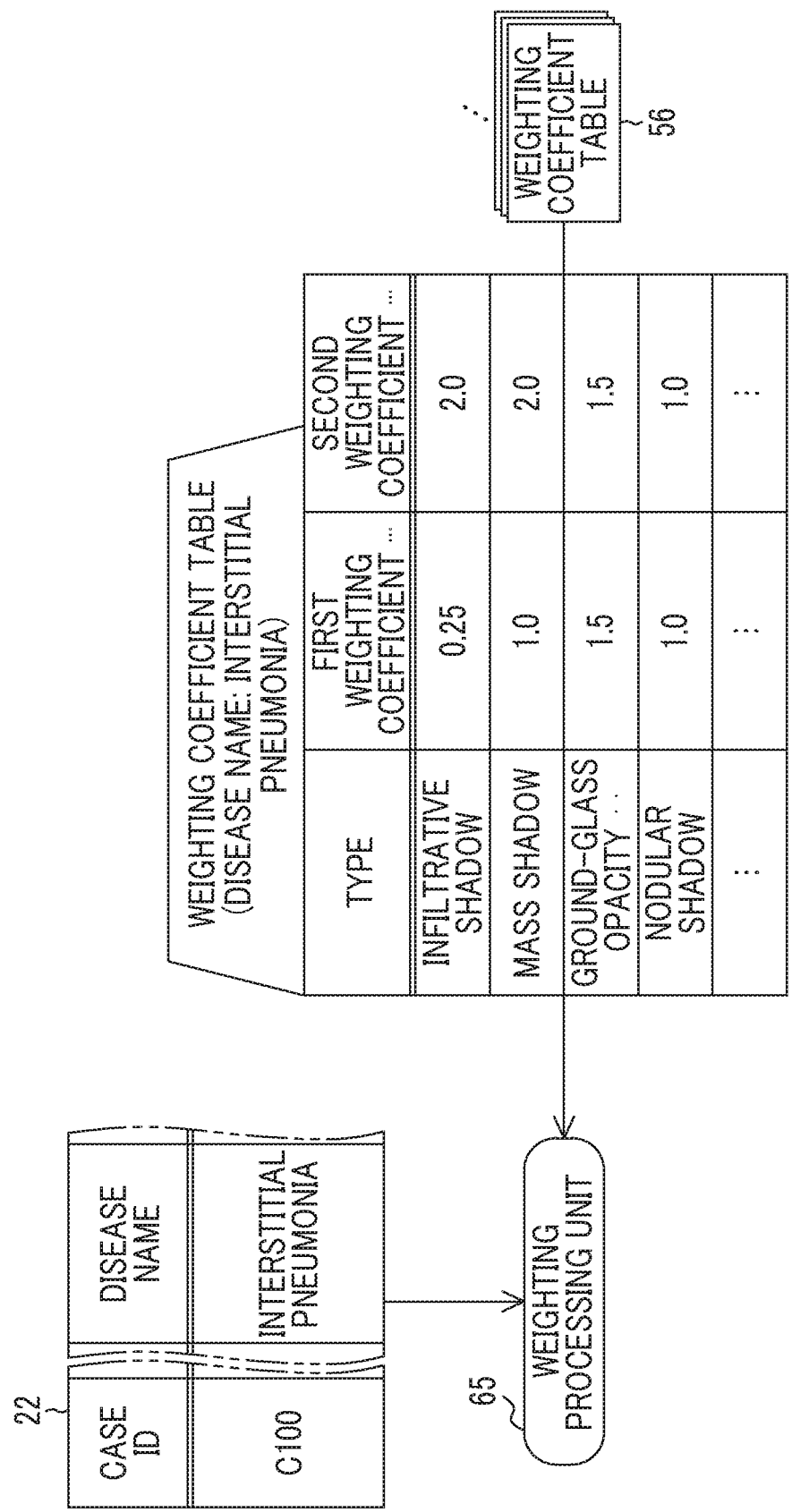
FIG. 13 is a diagram illustrating an aspect in which a weighting processing unit reads a weighting coefficient table corresponding to a disease name of a case.

As illustrated in FIG. 13, the weighting processing unit 65 reads the weighting coefficient table 56 having the same disease name as the disease name of the case 22 which is the source of the calculation of the individual lesion similarity LS to be subjected to the weighting processing from the storage device 45. Then, the processing unit 65 performs the weighting process using each of the weighting coefficients CF1 and CF2 registered in the read weighting coefficient table 56.

FIG. 13 illustrates a case in which the case 22 which is the source of the calculation of the individual lesion similarity LS to be subjected to the weighting processing is the case 22 with the case ID "C100" and interstitial pneumonia has been registered as the disease name as in FIG. 8. In this case, the weighting processing unit 65 reads the weighting coefficient table 56 for interstitial pneumonia illustrated in FIG. 9 from the storage device 45 and performs the weighting process using the read weighting coefficient table 56.

Figure 14:
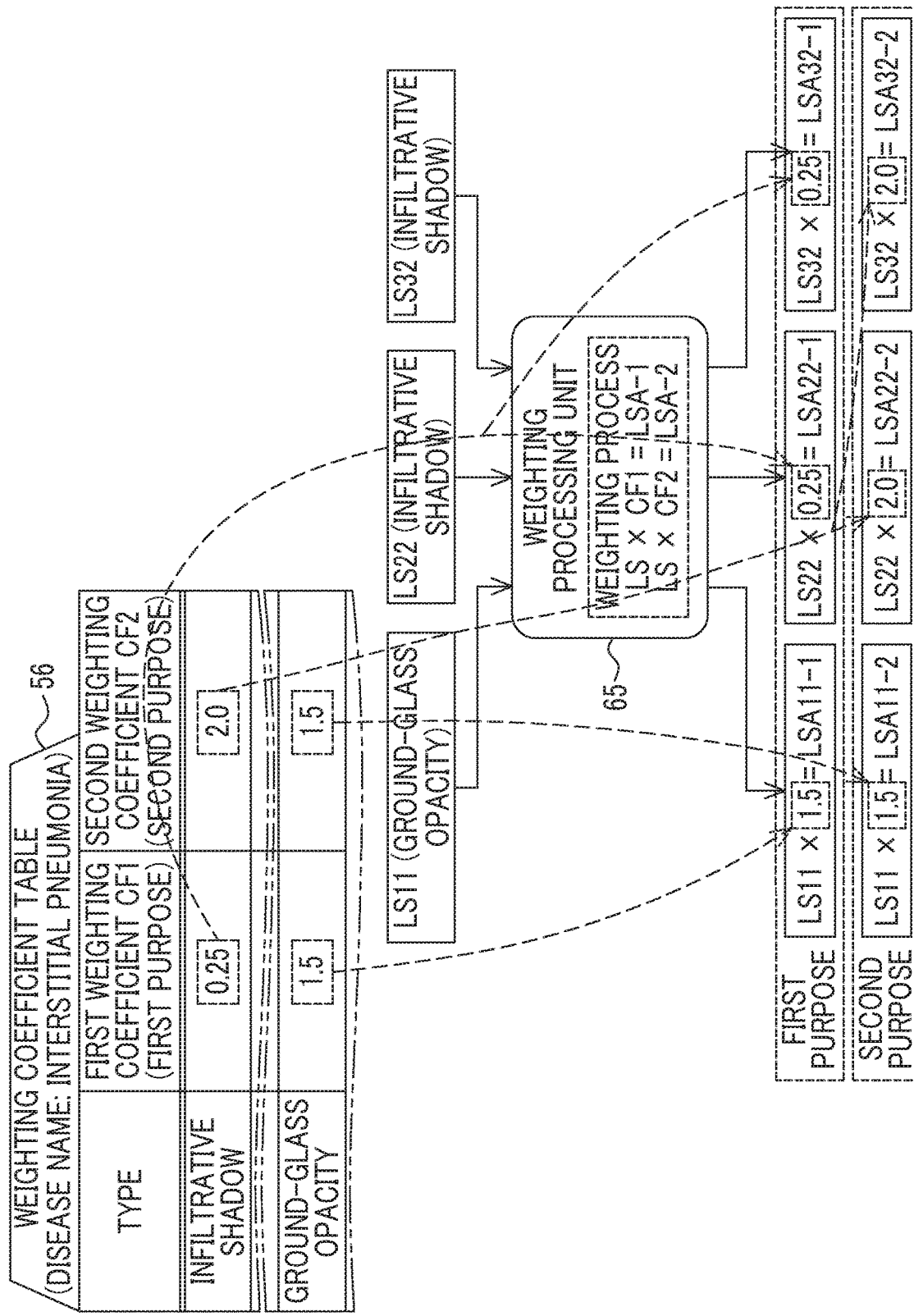
FIG. 14 is a diagram illustrating a weighting processing method.

In FIG. 14, the weighting processing unit 65 performs, as the weighting process, the following calculation of multiplying the individual lesion similarity LS by each of the weighting coefficients CF1 and CF2 to obtain the processed individual lesion similarities LSA-1 and LSA-2.

$$LS \times CF1 = LSA\text{-}1$$

$$LS \times CF2 = LSA\text{-}2$$

FIG. 14 illustrates an example of the weighting process for the case 22 with the case ID "C100" as in FIG. 8 and FIG. 13. In this case, the weighting processing unit 65 uses the weighting coefficient table 56 for interstitial pneumonia. Then, the weighting processing unit 65 multiplies the individual lesion similarity LS11 between the target lesion and the case lesion which are ground-glass opacity by a first weighting coefficient CF1 of 1.5 to calculate the processed individual lesion similarity LSA11-1. In addition, the weighting processing unit 65 multiplies the individual lesion similarity LS11 by a second weighting coefficient CF2 of 1.5 to calculate the processed individual lesion similarity LSA11-2. For the individual lesion similarities LS22 and LS32 between the target lesion and the case lesion which are infiltrative shadows, similarly, the weighting processing unit 65 multiplies the individual lesion similarities by a first weighting coefficient CF1 of 0.25 and a second weighting coefficient CF2 of 2.0 to calculate the processed individual lesion similarities LSA22-1, LSA22-2, LSA32-1, and LSA32-2. In the case of this example, the processed individual lesion similarities LSA11-1 and LSA11-2 have the same value and the values of the processed individual lesion similarities LSA22-2 and LSA32-2 are eight times the values of the processed individual lesion similarities LSA22-1 and LSA32-1.

Figure 15:
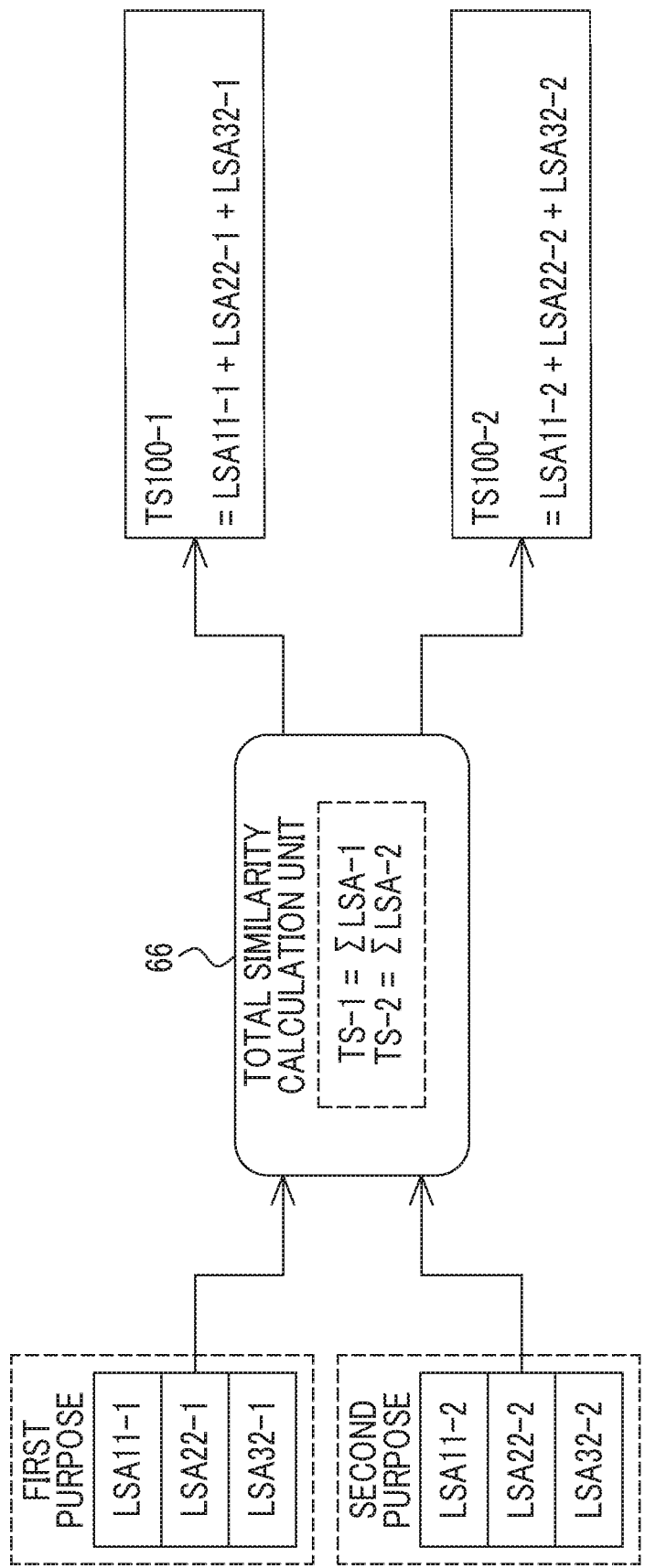
FIG. 15 is a diagram illustrating a method for calculating a total similarity.

In FIG. 15, the total similarity calculation unit 66 calculates a total similarity TS-1 corresponding to the first purpose and a total similarity TS-2 corresponding to the second purpose using the following expression.

$$TS\text{-}1 = \Sigma LSA\text{-}1$$

$$TS\text{-}2 = \Sigma LSA\text{-}2$$

FIG. 15 illustrates a method for calculating the total similarity with the case 22 with the case ID "C100", following FIG. 14. In this case, a total similarity TS100-1 corresponding to the first purpose and a total similarity TS100-2 corresponding to the second purpose are as follows.

$$TS100\text{-}1 = LSA11\text{-}1 + LSA22\text{-}1 + LSA32\text{-}1$$

$$TS100\text{-}2 = LSA11\text{-}2 + LSA22\text{-}2 + LSA32\text{-}2$$

The search unit 67 selects a case 22 satisfying a preset condition as the similar case. The preset condition is, for example, that the cases 22 having the total similarities TS-1 which rank first to twelfth are used as the similar cases. The condition may be defined not only by the ranking of the total similarities TS-1 but also by the ranking of the total similarities TS-2 or the ranking of the similarities obtained by adding the total similarities TS-1 and TS-2. Even in a case in which the cases 22 are the same, the values of the total similarities TS-1 and TS-2 are different from each other, which will be described below. Therefore, in the condition that the cases 22 having the total similarities TS-1 which rank first to twelfth are used as the similar cases, the cases 22 having the total similarities TS-2 which rank first to twelfth are not necessarily searched as the similar cases.

A table 80 illustrated in FIG. 16 shows an example of the similar cases selected by the search unit 67 on the basis of the condition that the cases 22 having the total similarities TS-1 which rank first to twelfth are used as the similar cases.

The table 80 shows a case in which the cases 22 having the total similarities TS-1 and TS-2 which rank first to twelfth are searched as the similar cases.

In the table 80, numbers on the left side of a dashed line in a ranking item are the rankings of the total similarities TS-1 and TS-2 (in ascending order). In contrast, numbers on the right side of the dashed line are the rankings (hereinafter, referred to as rankings in the same disease) of the total similarities TS-1 and TS-2 in the similar cases with the same disease name.

The case 22 with the total similarity TS-1 that ranks first is a case 22 with a case ID "C053" which has the lowest total similarity TS-1 of 9.1 (the highest similarity). Then, a case ID "C062" with a total similarity TS-1 of 12.5, a case ID "C005" with a total similarity TS-1 of 15.7, . . . rank in this order. In contrast, the case 22 with the total similarity TS-2 that ranks first is a case 22 with a case ID "C062" which has the lowest total similarity TS-2 of 10.3. Then, a case ID "C005" with a total similarity TS-2 of 11.9, a case ID "C001" with a total similarity TS-2 of 12.7, . . . rank in this order.

As such, the weighting process is performed using different weighting coefficients CF1 and CF2. Therefore, even in the same cases 22, the values of the total similarities TS-1 and TS-2 are different and the rankings thereof are naturally different. As the case 22 becomes a more effective clue to specify the disease name, the total similarity TS-1 becomes lower and the ranking thereof becomes higher. In contrast, as the case 22 becomes a more effective clue to specify the severity, the total similarity TS-2 becomes lower and the ranking thereof becomes higher.

For example, in the case of bacterial pneumonia, the rankings of the total similarities TS-1 in the same disease are in the order of the case ID "C005" with a total similarity TS-1 of 15.7, the case ID "C001" with a total similarity TS-1 of 17.2, and a case ID "C008" with a total similarity TS-1 of 20.8. For example, in the case of hypersensitive pneumonia, the rankings of the total similarities TS-2 in the same disease are in the order of the case ID "C062" with a total similarity TS-2 of 10.3, the case ID "C053" with a total similarity TS-2 of 13.1, and a case ID "C081" with a total similarity TS-2 of 16.5.

In FIG. 17, in a first list L1 created by the search unit 67, the similar cases are arranged in descending order of the ranking (hereinafter, referred to as a candidate disease ranking) of the diseases to be the candidates of the disease name by the doctor DR. The first list L1 has the items of a disease name, a total similarity TS-1 (representative value), and a case image (representative image). The total similarity TS-1 (representative value) is the value of the total similarity TS-1 of the similar case which ranks first in the same disease for each disease name (the value of the lowest total similarity TS-1 in the similar cases with the same disease name) The candidate disease ranking is the ranking of the disease name in ascending order of the total similarity TS-1 (representative value). As the ranking becomes higher, the disease name is more suitable as the candidate of the disease name specified by the doctor DR. The case image (representative image) is the case image 20C of the similar case having the total similarity TS-1 (representative value).

The first list L1 illustrated in FIG. 17 is created by the search unit 67 on the basis of the table 80 illustrated in FIG. 16. In this case, according to the table 80 illustrated in FIG. 16, the total similarity TS-1 (representative value) of the case ID "C005" is 15.7 for the disease name of bacterial pneumonia, the total similarity TS-1 of a case ID "C033" is 18.6 for the disease name of tuberculosis, the total similarity TS-1 of the case ID "C053" is 9.1 for the disease name of hypersensitive pneumonia, and the total similarity TS-1 of a case ID "C088" is 21.6 for the disease name of interstitial pneumonia. Therefore, for the candidate disease rankings, hypersensitive pneumonia ranks first, bacterial pneumonia ranks second, tuberculosis ranks third, and interstitial pneumonia ranks fourth.

In addition, the candidate disease rankings may be decided in descending order of the number of similar cases. In the table 80 illustrated in FIG. 16, there are three similar cases for each disease name and the numbers of similar cases for the disease names are equal to each other. Therefore, it is difficult to decide the candidate disease rankings on the basis of the number of similar cases. However, in a case in which there is a clear difference between the numbers of similar cases for each disease name, for example, in a case in which the number of similar cases of hypersensitive pneumonia is 20 while the number of similar cases of interstitial pneumonia is 2, it is effective to decide the candidate disease ranking in descending order of the number of similar cases.

The mean value of the total similarities TS-1 of the similar cases of the same disease name may be used as the total similarity TS-1 (representative value). In addition, the case image 20C of a similar case having the lowest total similarity TS-2 among the similar cases of the same disease name may be used as the case image (representative image).

In FIG. 18, in the second list L2 created by the search unit 67, the similar cases of each disease name are arranged in descending order of the ranking of the total similarity TS-2 in the same disease. The second list L2 includes the items of a case ID, a total similarity TS-2, severity, and a case image.

The second list L2 illustrated in FIG. 18 is created on the basis of the table 80 illustrated in FIG. 16 by the search unit 67 like the first list L1 illustrated in FIG. 17. In this case, according to the table 80 illustrated in FIG. 16, for example, for hypersensitive pneumonia, the ranking in the same disease is in the order of the case ID "C062" with a total similarity TS-2 of 10.3, the case ID "C053" with a total similarity TS-2 of 13.1, and the case ID "C081" with a total similarity TS-2 of 16.5.

Figure 19:
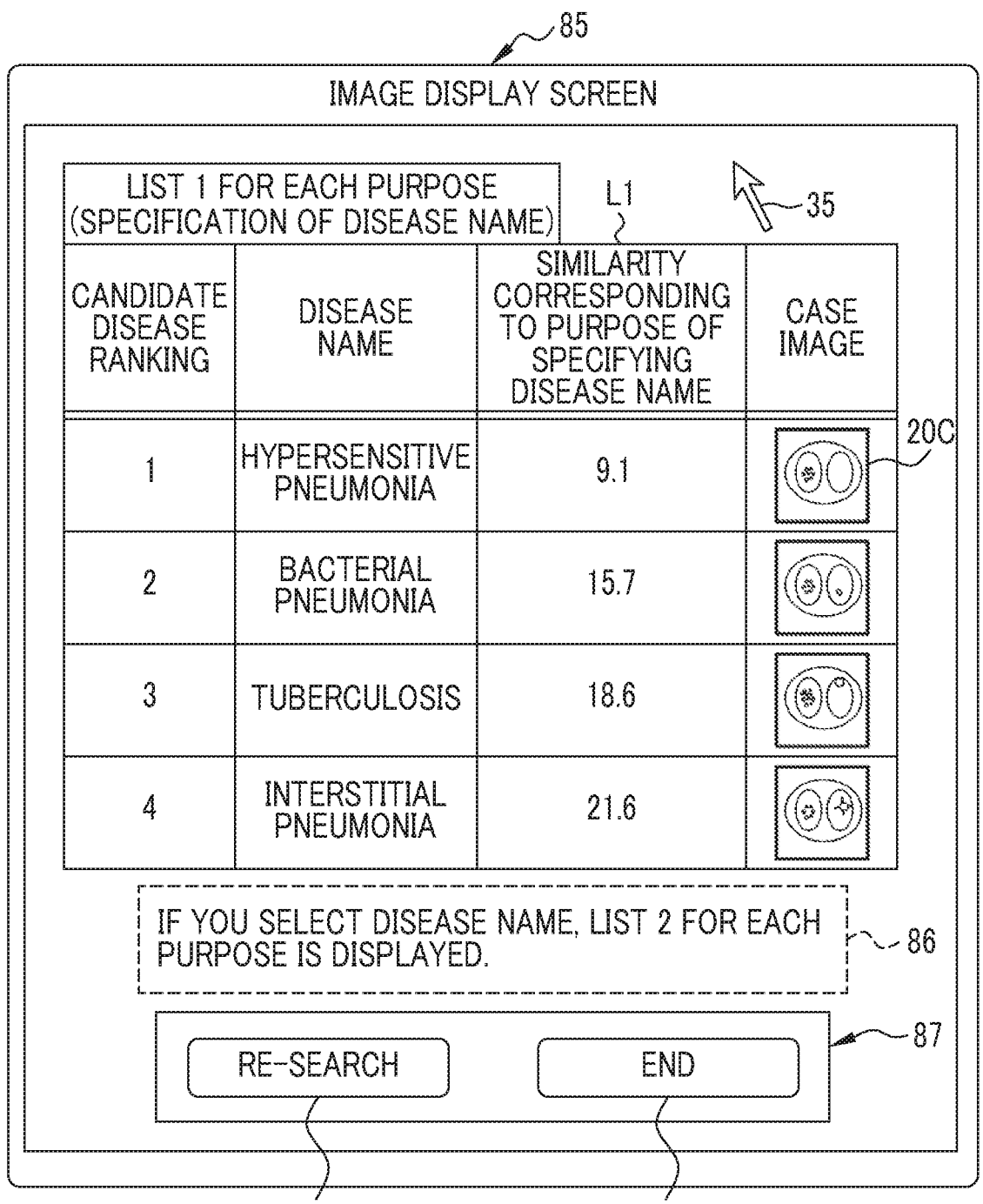
FIG. 19 is a diagram illustrating a list display screen on which the first list is displayed.

In FIG. 19, the first list L1 is displayed on the list display screen 85 which is first output to the treatment department terminal 12 by the screen output control unit 68. A message 86 indicating that it is possible to select a disease name in the first list L1 and the second list L2 is displayed in a case in which a disease name is selected is displayed below the first list L1. That is, the screen output control unit 68 displays the first list L1 such that the selection of one of the similar cases can be received.

The list display screen 85 further includes a button display region 87 provided below the message 86. The button display region 87 is provided with a re-search button 88 that is selected to return the image display screen 30 illustrated in FIG. 5 and re-searches for similar cases and an end button 89 that is selected to end the search of the similar cases.

FIG. 19 illustrates the list display screen 85 on which the first list L1 illustrated in FIG. 17 is displayed. In a case in which the number of similar cases is large and the first list L1 does not fit on the list display screen 85 at one time, a vertical scroll bar may be provided to vertically scroll the first list L1.

FIG. 20 illustrates the list display screen 85 in a case in which one of the similar cases in the first list L1 is selected. In this case, in addition to the first list L1, the second list L2 is displayed on the list display screen 85. As illustrated in FIG. 20, the second list L2 is displayed on the right side of the selected similar case in the form of a sticky note.

In the first list L1, the selected similar case has a larger vertical length than that in the list display screen 85 illustrated in FIG. 19 in order to display the second list L2 on the right side of the selected similar case. In contrast, the similar cases other than the selected similar case have a smaller vertical length than those in the list display screen 85 illustrated in FIG. 19 and only the rectangular frame of the case image (representative image) is displayed.

A close button 90 is provided at the upper right end of the second list L2. In a case in which the close button 90 is selected by the cursor 35, the display of the second list L2 is removed and the vertical length of each similar case returns to the original value. The display returns to the list display screen 85 illustrated in FIG. 19.

FIG. 20 illustrates a case in which hypersensitive pneumonia is selected by the cursor 35 as represented by hatching. The second list L2 illustrated in FIG. 20 is a portion corresponding to hypersensitive pneumonia extracted from the second list L2 illustrated in FIG. 18. The second list L2 may be displayed on a screen different from the screen on which the first list L1 is displayed. In addition, in a case in which the second list L2 does not fit on the list display screen 85 at one time as in the first list L1, a vertical scroll bar may be provided to vertically scroll the second list L2.

The case images 20C in the first list L1 or the second list L2 can be selected on the list display screen 85. In a case in which a case image 20C is selected, for example, the full-size case image 20C is displayed on a screen different from the list display screen 85.

Next, the operation of the similar case search server 17 having the above-mentioned configuration will be described with reference to FIG. 21. First, the operation program 55 is run. Then, the request receiving unit 60, the case acquisition unit 61, the lesion extraction unit 62, the feature amount calculation unit 63, the individual lesion similarity calculation unit 64, the weighting processing unit 65, the total similarity calculation unit 66, the search unit 67, the screen output control unit 68, and the weighting coefficient setting unit 69 are constructed in the CPU 47 and the computer forming the similar case search server 17 functions as the similar case search apparatus.

The doctor DR browses the target image 20T on the image display screen 30 in the treatment department terminal 12, designates the region of interest ROI, and selects the similar case search button 38. Then, a request to search for similar cases having the case image 20C similar to the target image 20T is transmitted to the similar case search server 17.

As illustrated in Step SD10 of FIG. 21, in the similar case search server 17, the request receiving unit 60 receives the similar case search request from the treatment department terminal 12. A notification indicating that the similar case search request has been received is output from the request receiving unit 60 to the case acquisition unit 61. In addition, the similar case search request is output from the request receiving unit 60 to the lesion extraction unit 62.

The case acquisition unit 61 outputs a request to acquire the case 22 to the case DB server 16. Then, the case acquisition unit 61 acquires the case 22 transmitted from the case DB server 16 in response to the acquisition request (Step SD11). That is, the type of case lesion and the feature amount ZC included in the case 22 are acquired (a second type acquisition step and a second feature amount acquisition step). The case 22 is output from the case acquisition unit 61 to the individual lesion similarity calculation unit 64 and the weighting coefficient setting unit 69.

The similar case search request includes the region information 25 of the region of interest ROI. The lesion extraction unit 62 performs image analysis for the region of interest ROI indicated by the region information 25 to extract a target lesion in the region of interest ROI (Step SD12). While the target lesion is being extracted, the type of target lesion is specified. That is, the type of target lesion is acquired (first type acquisition step). The extraction result of the target lesion is output from the lesion extraction unit 62 to the feature amount calculation unit 63 and the individual lesion similarity calculation unit 64.

The feature amount calculation unit 63 calculates the feature amount ZT of the target lesion (Step SD13). That is, the feature amount ZT of the target lesion is acquired (first feature amount acquisition step). The feature amount ZT of the target lesion is output from the feature amount calculation unit 63 to the individual lesion similarity calculation unit 64.

Then, as illustrated in FIG. 8, the individual lesion similarity calculation unit 64 calculates the individual lesion similarity LS (Step SD14, an individual lesion similarity calculation step). The individual lesion similarity LS is output from the individual lesion similarity calculation unit 64 to the weighting processing unit 65.

The weighting processing unit 65 performs the weighting process for the individual lesion similarity LS (Step SD15, a weighting processing step). Specifically, as illustrated in FIG. 13, the weighting processing unit 65 reads the weighting coefficient table 56 having the same disease name as the disease name of the case 22 which is the source of the calculation of the individual lesion similarity LS to be subjected to the weighting process from the storage device 45.

Then, as illustrated in FIG. 14, the weighting process is performed using the first weighting coefficient CF1 corresponding to the degree of contribution of each type of lesion to the specification of the disease name to calculate the processed individual lesion similarity LSA-1 corresponding to the first purpose of specifying the disease name. In addition, the weighting process is performed using the second weighting coefficient CF2 corresponding to the degree of contribution of each type of lesion to the specification of the severity to calculate the processed individual lesion similarity LSA-2 corresponding to the second purpose of specifying the severity. The processed individual lesion similarities LSA-1 and LSA-2 are output from the weighting processing unit 65 to the total similarity calculation unit 66.

As such, the weighting process is performed for the individual lesion similarity LS using the weighting coefficient considering the purpose of the similar case. Therefore, for the first purpose of specifying the disease name, a similar case, from which an effective clue to specify the disease name is obtained, is easily searched. For the second purpose of specifying the severity, a similar case, from which an effective clue to specify the severity is obtained, is easily searched. As a result, it is possible to obtain the similar cases from which an effective clue corresponding to the purpose is obtained, that is, the similar cases desired by the doctor DR.

The doctor DR mainly searches for the similar cases in a case in which the doctor DR specifies the disease name and a case in which the doctor DR specifies the severity. In this example, the weighting process is performed using each of the weighting coefficients CF1 and CF2 corresponding to the two purposes of the similar cases. Therefore, it is possible to provide similar cases suitable for the main reference purpose to the doctor DR and to effectively support the specification of the disease name and the severity by the doctor DR.

Since the weighting coefficient table 56 is provided for each disease (the weighting coefficient is set for each disease), it is possible to perform a more detailed weighting process than that in a case in which the weighting process is performed using a uniform weighting coefficient regardless of the disease.

As illustrated in FIG. 11, the first weighting coefficient CF1 is set on the basis of the first likelihood ratio LR1 which is a statistical index indicating the likelihood of a specific disease in a case in which a specific type of lesion is present. In addition, as illustrated in FIG. 12, the second weighting coefficient CF2 is set on the basis of the second likelihood ratio LR2 which is a statistical index indicating the likelihood of a specific disease being a severe disease in a case in which a specific type of lesion is present. According to each of the set weighting coefficients CF1 and CF2, for example, in a case in which the first likelihood ratio LR1 is low and the type of lesion is not helpful in specifying the disease name, the value of the first weighting coefficient CF1 is small. On the contrary, in a case in which the first likelihood ratio LR1 is high and the type of lesion is helpful in specifying the disease name, the value of the first weighting coefficient CF1 is large. Therefore, it is possible to perform an appropriate weighting process.

In addition, the doctor DR may set each of the weighting coefficients CF1 and CF2 on the basis of, for example, his or her own medical knowledge and experience. However, in this case, there is a concern that an appropriate weighting process will not be performed because the doctor DR subjectively sets the weighting coefficients CF1 and CF2. In addition, it is very troublesome for the doctor DR to manually set the weighting coefficients CF1 and CF2. Therefore, as in this example, it is preferable to set the weighting coefficients CF1 and CF2 on the basis of an objective index such as the likelihood ratio LR.

As illustrated in FIG. 15, the total similarity calculation unit 66 calculates the total similarity TS-1 corresponding to the first purpose on the basis of the processed individual lesion similarity LSA-1 and calculates the total similarity TS-2 corresponding to the second purpose on the basis of the processed individual lesion similarity LSA-2 (Step SD16, a total similarity calculation step). The total similarities TS-1 and TS-2 are output from the total similarity calculation unit 66 to the search unit 67.

The search unit 67 searches for similar cases on the basis of the total similarities TS-1 and TS-2 and creates the first list L1 and the second list L2 on the basis of the searched similar cases (Step SD17, a search step). The first list L1 and the second list L2 are output from the search unit 67 to the screen output control unit 68.

The screen output control unit 68 outputs the list display screen 85 to the treatment department terminal 12 (Step SD18). The first list L1 illustrated in FIG. 19 is displayed on the list display screen 85 that is output first. The doctor DR browses the first list L1 and specifies the disease name of the patient whose target image 20T has been captured, on the basis of the candidate disease ranking or the disease name in the first list L1.

In a case in which one of the similar cases in the first list L1 is selected, the second list L2 is displayed as illustrated in FIG. 20. The doctor DR browses the second list L2 and specifies the severity of the patient whose target image 20T has been captured, on the basis of the ranking in the same disease or the severity in the second list L2.

Since the first list L1 and the second list L2 are separately created and displayed, it is possible to display similar cases corresponding to the purpose. In addition, in a case in which the first list L1 is displayed on the first list display screen 85 and one of the similar cases in the first list L1 is selected, the second list L2 is displayed. Therefore, it is possible to match the thought process of the doctor DR specifying the disease name first and then specifying the severity with the display of the similar cases.

In addition, the first list L1 and the second list L2 may be displayed at the same time. However, in this case, the display may be mixed up and it is difficult to understand the lists. As a result, there is a concern that the doctor DR will be confused. For this reason, it is preferable to separately display the first list L1 and the second list L2 as in this example.

One similar case search operation is ended by the above-mentioned Steps SD10 to SD18. In a case in which the doctor DR wants to perform the similar case search, the doctor DR selects the re-search button 88 on the list display screen 85. In a case in which the doctor DR wants to end the similar cases search, the doctor DR selects the end button 89.

In the above-described embodiment, the number of cases 22 is counted and the first relational table 75A is created in two options, that is, a case in which a specific type of case lesion is present and a case in which a specific type of case lesion is absent. However, the invention is not limited thereto. As in a first relational table 95A illustrated in FIG. 22, two or more options may be used by classifying the cases according to the size (area) of the case lesion.

Similarly to the first relational table 75A according to the above-described embodiment, the first relational table 95A corresponds to a case in which the type of lesion is an infiltrative shadow and the disease name is interstitial pneumonia. However, the first relational table 95A is different from the first relational table 75A in that the cases in which there is an infiltrative shadow are classified into three options, that is, a case in which a large infiltrative shadow is present, a case in which a medium infiltrative shadow is present, and a case in which a small infiltrative shadow is present. In addition, an abstract expression is used for convenience of description. However, in practice, each option is defined by the numerical range of the area.

In this case, the first likelihood ratio LR1 is calculated for each of the three options as illustrated in a table 96 below the first relational table 95A. For example, the first likelihood ratio LR1 in a case in which a large infiltrative shadow is present is calculated as follows.

$$LR1 = \{A1/(A1 + A2 + A3 + A4)\}/\{B1/(B1 + B2 + B3 + B4)\} =$$
$$\{2/(2 + 6 + 12 + 30)\}/\{44/(44 + 16 + 10 + 10)\} \approx 0.07$$

Similarly, the first likelihood ratio LR1 in a case in which a medium infiltrative shadow is present is 0.6. The first likelihood ratio LR1 in a case in which a small infiltrative shadow is present is 1.92.

In this case, items classified according to the size are added to a weighting coefficient table 97 and the first weighting coefficient CF1 that is based on the first likelihood ratio LR1 calculated for each option is registered in the weighting coefficient table 97. As described above, the first likelihood ratio LR1 in a case in which a large infiltrative shadow is present is about 0.07. Therefore, the first weighting coefficient CF1 in a case in which a large infiltrative shadow is present is 0.25 with reference to the substitution table 76 illustrated in FIGS. 11 and 12. Similarly, the first weighting coefficient CF1 in a case in which a medium infiltrative shadow is present is 0.5 and the first weighting coefficient CF1 in a case in which a large infiltrative shadow is present is 1.0.

In a case in which the weighting process is performed using the weighting coefficient table 97, one of the three large, medium, and small first weighting coefficients CF1 is selectively used according to the size of at least one of the target lesion or the case lesion whose individual lesion similarity LS is to be calculated.

As such, in a case in which items are classified according to the size of the case lesion to increase the number of options, the first likelihood ratio LR1 is calculated for each option, and the first weighting coefficient CF1 is set for each option, it is possible to perform a more detailed weighting process.

For the second relational table 75B, instead of the configuration according to the above-described embodiment in which the number of cases 22 is counted and the relational table is created according to two options, that is, a case in which a specific type of case lesion is present and a case in which a specific type of case lesion is absent, items may be classified according to the size of the case lesion to increase options, which is not illustrated. In the above-described embodiment, the severity is divided into two options, that is, a case in which the disease is a severe disease and a case in which the disease is not a severe disease. However, the case in which the disease is a severe disease may be divided into a plurality of levels such as severe disease level 1 and severe disease level 2.

In the above-described embodiment, the aspect in which the doctor DR designates the region of interest ROI has been described. However, image analysis may be performed for the target image 20T and the region of interest ROI in which the presence of the target lesion is suspected may be automatically designated.

In the above-described embodiment, the distance between the feature vector having the feature amount ZTi of the target lesion as an element and the feature vector having the feature amount ZCi of the case lesion as an element is calculated as the individual lesion similarity LS. However, a correlation coefficient between the feature amount ZTi of the target lesion and the feature amount ZCi of the case lesion may be calculated as the individual lesion similarity LS. In this case, contrary to the above-described embodiment, as the value of the individual lesion similarity LS (correlated with the feature amount ZTi and the feature amount ZCi) becomes larger, the similarity between the target lesion and the case lesion becomes higher.

In addition, in a case in which the individual lesion similarity LS is calculated, a combination of this embodiment and the method disclosed in JP2016-045662A may be used. The method disclosed in JP2016-045662A calculates the first existence probability of a specific type of lesion existing in the target image 20T using a statistical method. Then, the method calculates, as the similarity, at least one of the coexistence probability of a specific type of lesion existing in both the target image 20T and the case image 20C or the non-coexistence probability of a specific type of lesion existing independently only in one of the target image 20T and the case image 20C on the basis of the first existence probability and the second existence probability of a specific type of lesion existing in the case image 20C which is calculated by the same method as the first existence probability. In a case in which this method is combined, it is possible to further improve the accuracy of the individual lesion similarity LS.

The individual lesion similarity LS may be multiplied by a coefficient (hereinafter, referred to as a size coefficient) SS corresponding to the size of the lesion separately from the weighting coefficients CF1 and CF2. The size coefficient SS is, for example, the proportion of the region of the target lesion to the target image 20T. Alternatively, the larger of the proportion of the target lesion to the target image 20T and the proportion of the case lesion to the case image 20C may be used as the size coefficient SS.

For example, it is considered that the size coefficient of the target lesion and the case lesion with the lesion ID "L001" which are ground-glass opacity illustrated in FIG. 8 is SS11, the size coefficient of the target lesion and the case lesion with the lesion ID "L002" which is an infiltrative shadow is SS22, and the size coefficient of the target lesion with the lesion ID "L003" and the case lesion with the lesion ID "L002" which are infiltrative shadows is SS32.

In this case, the individual lesion similarities LS obtained by multiplying each processed individual lesion similarity LSA illustrated in FIG. 14 by the size coefficients SS, that is, LSA11-1×SS11, LSA11-2×SS11, LSA22-1×SS22, LSA22-2×SS22, LSA32-1×SS32, and LSA32-2×SS32 are finally output to the total similarity calculation unit 66. As such, one index of a visual similarity (image similarity), such as the size of the lesion, can be reflected in the individual lesion similarity LS by multiplying the individual lesion similarity LS by the size coefficient SS.

In the above-described embodiment, the type of case lesion and the feature amount ZC are specified and calculated before similar cases are searched and the case 22 including the type of case lesion and the feature amount ZC is stored in the case DB 23. However, whenever similar cases are searched, the lesion extraction unit 62 may specify the type of case lesion and the feature amount calculation unit 63 may calculate the feature amount ZC, using the same method as that for specifying and calculating the type of target lesion and the feature amount ZT. In this case, the type of case lesion and the feature amount ZC do not need to be included in the case 22. Further, in this case, the lesion extraction unit 62 corresponds to the second type acquisition unit that acquires the type of case lesion and the feature amount calculation unit 63 corresponds to the second feature amount acquisition unit that acquires the feature amount ZC of the case lesion.

In addition, the similar case search may be performed in consideration of other information, such as the measurement results of vital signs, the results of blood tests, and findings obtained at the time of a medical interview described in the electronic medical record.

In the above-described embodiment, the similar case search apparatus according to the invention has been described in the form of the similar case search server 17 which performs similar case search on the basis of the similar case search request from the treatment department terminal 12. However, the treatment department terminal 12 may have the functions of the similar case search apparatus. In this case, for example, each unit, such as the weighting processing unit 65, is constructed in the CPU of the treatment department terminal 12 and the treatment department terminal 12 accesses the case DB server 16 and acquires the case 22.

The examination image DB server 15, the case DB server 16, and the similar case search server 17 may be separate servers as in the above-described embodiment or may be integrated into one server.

The similar case search server 17 may be configured by a plurality of server computers which are separated as hardware in order to improve processing capability or reliability. For example, a plurality of server computers dispersively take charge of each unit in such a manner that a server computer serves the functions of the request receiving unit 60 and the case acquisition unit 61, a server computer serves the functions of the lesion extraction unit 62 and the feature amount calculation unit 63, a server computer serves the functions of the individual lesion similarity calculation unit 64, the weighting processing unit 65, and the total similarity calculation unit 66, and a server computer serves the functions of the search unit 67, the screen output control unit 68, and the weighting coefficient setting unit 69.

As such, the hardware configuration of the computer system can be appropriately changed according to the required performances, such as processing capability, safety, and reliability. In addition to hardware, an AP, such as the operation program 55, may be duplicated or dispersively stored in a plurality of storage devices in order to ensure safety or reliability.

In the above-described embodiment, the medical information system 2 is constructed in the medical facility and the similar case search server 17 is used in one medical facility. However, the similar case search server 17 may be used by a plurality of medical facilities.

In the above-described embodiment, a client terminal, such as the treatment department terminal 12 provided in one medical facility, is connected to the similar case search server 17 through the network 18, such as a LAN, so as to communicate with the similar case search server 17 and the similar case search server 17 provides an application service, such as similar case search, in response to a request from the client terminal. However, the similar case search server 17 may be used by a plurality of medical facilities. In order to achieve the configuration, the similar case search server 17 is connected to the client terminals provided in a plurality of medical facilities through a wide area network (WAN), such as the Internet or a public communication network, so as to communicate with the client terminals. Then, the similar case search server 17 receives a request from each of the client terminals in the plurality of medical facilities through the WAN, such as the Internet or a public communication network, and provides an application service, such as similar case search, to each of the client terminals. In a case in which the WAN is used, it is preferable that a virtual private network (VPN) is constructed or a communication protocol having a high security level, such as Hypertext Transfer Protocol Secure (HTTPS), is used in consideration of information security.

In this case, the installation place and the operation subject of the similar case search server 17 may be, for example, a data center operated by a company different from the medical facility or may be one of a plurality of medical facilities.

The invention is not limited to the above-described embodiment and may use various configuration, without departing from the scope and spirit of the invention.

For example, one target image 20T or a plurality of target images 20T may be included in the similar case search request. In the case of the plurality of target images 20T, the region information 25 is added to each target image 20T. In addition, an image captured by the modality 13, such as an ultrasound probe, an electronic endoscope, or mammography, other than the CT apparatus described in the above-described embodiment may be used as the examination image 20.

In the above-described embodiment, the similar case search request including the entire target image 20T and the region information 25 is given as an example. However, instead of the entire target image 20T, an ROI image obtained by cutting out a portion of the region of interest ROI may be included in the similar case search request. In this case, the region information 25 does not need to be included in the similar case search request. As such, the entire target image 20T or a partial image cut out from the target image 20T may be included in the similar case search request.

An apparatus different from the similar case search server 17 may specify the type of target lesion and calculate the feature amount ZT and the similar case search server 17 may only acquire the type of target lesion and the feature amount ZT.

The output form of the first list L1 and the second list L2 is not limited to the list display screen 85 described in the above-described embodiment and includes printing out to a paper medium and the output of a file by, for example, electronic mail.

In the above-described embodiment, the hardware structure of processing units for performing various processes, such as the request receiving unit 60, the case acquisition unit 61, the lesion extraction unit 62, the feature amount calculation unit 63, the individual lesion similarity calculation unit 64, the weighting processing unit 65, the total similarity calculation unit 66, the search unit 67, the screen output control unit 68, and the weighting coefficient setting unit 69, is, for example, the CPU 47 which is a general-purpose processor that executes software (operation program 55) to function as various processing units, as described above.

Instead of some or all of the functions implemented by the CPU 47, the following various processors may be used. The various processors include, for example, a programmable logic device (PLD), such as a field-programmable gate array (FPGA), which is a processor whose circuit configuration can be changed after manufacture and a dedicated electric circuit, such as an application specific integrated circuit (ASIC), which is a processor having a dedicated circuit configuration designed to perform a specific process. Specifically, the hardware structure of the various processors is an electric circuit (circuitry) obtained by combining circuit elements such as semiconductor elements.

It is possible to understand the invention described in the following supplementary note from the above description.

[Supplementary Note 1]

There is provided a similar case search apparatus that searches for a similar case including a case image similar to a target image which is a medical examination target from a plurality of cases including the case image. The similar case search apparatus comprises: a first type acquisition processor that acquires a type of target lesion which is a lesion present in the target image; a second type acquisition processor that acquires a type of case lesion which is a lesion present in the case image; a first feature amount acquisition processor that acquires a feature amount of the target lesion; a second feature amount acquisition processor that acquires a feature amount of the case lesion; an individual lesion similarity calculation processor that calculates an individual lesion similarity which is a similarity between the target lesion and the case lesion of the same type on the basis of the feature amount of the target lesion and the feature amount of the case lesion; a weighting processing processor that performs a weighting process for the individual lesion similarity, using weighting coefficients which are preset for each of the types and a plurality of purposes; a total similarity calculation processor that calculates a total similarity between the target image and the case image for each of the purposes on the basis of the individual lesion similarity subjected to the weighting process; and a search processor that searches for the similar case on the basis of the total similarity.

The above-described various embodiments and various modification examples may be combined with each other. In addition, the invention is applied to a storage medium storing the program in addition to the program.

EXPLANATION OF REFERENCES

2: medical information system
10: treatment department
11: examination department
12: treatment department terminal
13: modality
14: order management terminal
15: examination image database (DB) server
16: case database (DB) server
17: similar case search server (similar case search apparatus)
18: network
19: similar case search system
20: examination image
20C: case image
20T: target image
21: examination image database (DB)
22: case
23: case database (DB)
25: region information
30: image display screen
31: input box
32: image display region
33, 87: button display region
34: search button
35: cursor
36: region designation button
37: designation clear button
38: similar case search button
45: storage device
46: memory
47: CPU
48: communication unit
49: data bus
55: operation program
56, 97: weighting coefficient table
60: request receiving unit
61: case acquisition unit (second type acquisition unit, second feature amount acquisition unit)
62: lesion extraction unit (first type acquisition unit)
63: feature amount calculation unit (first feature amount acquisition unit)
64: individual lesion similarity calculation unit
65: weighting processing unit
66: total similarity calculation unit
67: search unit
68: screen output control unit
69: weighting coefficient setting unit
75A, 95A: first relational table
75B: second relational table
76: substitution table
80: similar case search result table
85: list display screen
86: message
88: re-search button
89: end button
90: close button
96: first likelihood ratio table
DR: doctor
ROI: region of interest
Z, ZC, ZT: feature amount
LS: individual lesion similarity
LSA-1, LSA-2: processed individual lesion similarity
TS-1, TS-2: total similarity
L1: first list
L2: second list
CF1, CF2: first and second weighting coefficients
LR1, LR2: first and second likelihood ratios
SA1 to SA11, SB10 to SB12, SC10 to SC12, SD10 to SD18: step

What is claimed is:

1. A similar case search apparatus that searches for similar cases including a case image similar to a target image which is a medical examination target from a plurality of cases including the case image, comprising:
    a processor configured to:
        acquire a type of target lesion which is a lesion present in the target image;
        acquire a type of case lesion which is a lesion present in the case image;
        acquire a feature amount of the target lesion;
        acquire a feature amount of the case lesion;
        calculate an individual lesion similarity which is a similarity between the target lesion and the case lesion of the same type on the basis of the feature amount of the target lesion and the feature amount of the case lesion;
        perform a weighting process for the individual lesion similarity, using weighting coefficients which are preset for each of the types and a plurality of purposes;
        calculate a total similarity between the target image and the case image for each of the purposes on the basis of the individual lesion similarity subjected to the weighting process; and
        search for a similar case on the basis of the total similarity for at least one of the purposes,
    wherein the purposes include a purpose of specifying a disease name and a purpose of specifying a severity of a disease, and
    the processor is further configured to:
        perform the weighting process, using a first weighting coefficient which is the weighting coefficient corresponding to a degree of contribution of each type to the specification of the disease name, and
        perform the weighting process, using a second weighting coefficient which is the weighting coefficient corresponding to a degree of contribution of each type to the specification of the severity.

2. The similar case search apparatus according to claim 1, wherein the weighting coefficients for the types and the purposes are set for each disease.

3. The similar case search apparatus according to claim 1, wherein the case includes the disease name, and
    the first weighting coefficient is set on the basis of a first likelihood ratio obtained by statistically analyzing a causal relationship between the case lesion and the disease name included in the case.

4. The similar case search apparatus according to claim 1, wherein the case includes the severity, and
    the second weighting coefficient is set on the basis of a second likelihood ratio obtained by statistically analyzing a causal relationship between the case lesion and the severity included in the case.

5. The similar case search apparatus according to claim 1, wherein the processor is further configured to create a list of the searched similar cases for each of the purposes.

6. The similar case search apparatus according to claim 5, wherein the processor is further configured to:
output a list display screen for displaying the list,
display a first list which is the list corresponding to a first purpose and from which one of the similar cases is selected, and
display a second list which is the list corresponding to a second purpose in a case in which one of the similar cases in the first list is selected on the list display screen.

7. The similar case search apparatus according to claim 6, wherein the first purpose is to specify a disease name and the second purpose is to specify the severity of a disease.

8. The similar case search apparatus according to claim 7, wherein the similar cases are arranged in the first list according to a candidate disease ranking which is a ranking of the disease names included in the similar cases on the basis of the total similarity corresponding to the first purpose, and
the similar cases are arranged in the second list according to a ranking in the same disease which is a ranking of the total similarity corresponding to the second purpose in the similar cases of the same disease name.

9. A method for operating a similar case search apparatus that searches for similar cases including a case image similar to a target image which is a medical examination target from a plurality of cases including the case image, the method comprising:
a first type acquisition step of acquiring a type of target lesion which is a lesion present in the target image;
a second type acquisition step of acquiring a type of case lesion which is a lesion present in the case image;
a first feature amount acquisition step of acquiring a feature amount of the target lesion;
a second feature amount acquisition step of acquiring a feature amount of the case lesion;
an individual lesion similarity calculation step of calculating an individual lesion similarity which is a similarity between the target lesion and the case lesion of the same type on the basis of the feature amount of the target lesion and the feature amount of the case lesion;
a weighting processing step of performing a weighting process for the individual lesion similarity, using weighting coefficients which are preset for each of the types and a plurality of purposes;
a total similarity calculation step of calculating a total similarity between the target image and the case image for each of the purposes on the basis of the individual lesion similarity subjected to the weighting process; and a search step of searching for a similar case on the basis of the total similarity for at least one of the purposes,
wherein the purposes include a purpose of specifying a disease name and a purpose of specifying a severity of a disease, and
the method further comprises:
performing the weighting process, using a first weighting coefficient which is the weighting coefficient corresponding to a degree of contribution of each type to the specification of the disease name, and
performing the weighting process, using a second weighting coefficient which is the weighting coefficient corresponding to a degree of contribution of each type to the specification of the severity.

10. A similar case search system including a similar case search apparatus that searches for similar cases including a case image similar to a target image which is a medical examination target from a plurality of cases including the case image and a client terminal that is connected to the similar case search apparatus by a network and is operated by a doctor, the system comprising:
a processor is configured to:
acquire a type of target lesion which is a lesion present in the target image;
acquire a type of case lesion which is a lesion present in the case image;
acquire a feature amount of the target lesion;
acquire a feature amount of the case lesion;
calculate an individual lesion similarity which is a similarity between the target lesion and the case lesion of the same type on the basis of the feature amount of the target lesion and the feature amount of the case lesion;
perform a weighting process for the individual lesion similarity, using weighting coefficients which are preset for each of the types and a plurality of purposes;
calculate a total similarity between the target image and the case image for each of the purposes on the basis of the individual lesion similarity subjected to the weighting process; and
search for a similar case on the basis of the total similarity for at least one of the purposes,
wherein the purposes include a purpose of specifying a disease name and a purpose of specifying a severity of a disease, and
the processor is further configured to:
perform the weighting process, using a first weighting coefficient which is the weighting coefficient corresponding to a degree of contribution of each type to the specification of the disease name, and
perform the weighting process, using a second weighting coefficient which is the weighting coefficient corresponding to a degree of contribution of each type to the specification of the severity.

* * * * *